(12) United States Patent
Blamire et al.

(10) Patent No.: US 11,887,308 B2
(45) Date of Patent: Jan. 30, 2024

(54) SYSTEM FOR PROCESSING IMAGES TO DETECT PROPERTIES OF SKELETAL MUSCLE

(71) Applicant: UNIVERSITY OF NEWCASTLE UPON TYNE, Newcastle (GB)

(72) Inventors: Andrew Blamire, Newcastle (GB); Ian Schofield, Newcastle (GB); Roger Whittaker, Newcastle (GB)

(73) Assignee: UNIVERSITY OF NEWCASTLE UPON TYNE, Newcastle (GB)

( * ) Notice: Subject to any disclaimer, the term of this patent is extended or adjusted under 35 U.S.C. 154(b) by 587 days.

(21) Appl. No.: 17/057,767

(22) PCT Filed: May 9, 2019

(86) PCT No.: PCT/GB2019/051271
§ 371 (c)(1),
(2) Date: Nov. 23, 2020

(87) PCT Pub. No.: WO2019/229413
PCT Pub. Date: Dec. 5, 2019

(65) Prior Publication Data
US 2021/0104045 A1    Apr. 8, 2021

(30) Foreign Application Priority Data
May 31, 2018    (GB) .................................... 1808950

(51) Int. Cl.
*A61B 5/055*    (2006.01)
*G06T 7/00*    (2017.01)
(Continued)

(52) U.S. Cl.
CPC ............ *G06T 7/0016* (2013.01); *A61B 5/055* (2013.01); *A61B 5/4076* (2013.01);
(Continued)

(58) Field of Classification Search
CPC ... A61B 5/1101; A61B 5/1124; A61B 5/4082; A61B 5/055; A61B 5/4076;
(Continued)

(56) References Cited

U.S. PATENT DOCUMENTS 10,493,272 B1 *  12/2019  Feinstein .............. A61N 1/323
10,758,732 B1 *   9/2020  Heldman ............... A61B 5/291
(Continued)

FOREIGN PATENT DOCUMENTS

| CN | 106202739 A | 12/2016 |
|----|-------------|---------|
| JP | 2002-209868 A | 7/2002 |
| JP | 2011-030991 A1 | 2/2011 |

OTHER PUBLICATIONS

International Preliminary Report on Patentability for International Application No. PCT/GB2019/051271, dated Dec. 10, 2020.
(Continued)

*Primary Examiner* — Cindy Trandai
(74) *Attorney, Agent, or Firm* — Jason H. Vick; Sheridan Ross, PC

(57) ABSTRACT

Machine readable instructions, a data processing apparatus and a method are provided to determine one or more properties of motor units of skeletal muscle by analyzing a time series of Magnetic Resonance, MR, images representing a slice of a body part to identify signal voids in one or more images of the series. A comparison of at least one characteristic of the identified signal voids in the images is performed with a control data set of MR images produced by applying a controlled stimulus to a motor nerve to establish inherent characteristics of signal voids corresponding to motor units of skeletal muscle. Properties of candidate motor units are analyzed to confirm or reject them as motor units and at least one of: a firing frequency of at least one of the confirmed motor units, a size of at least one of the confirmed motor units, a number of confirmed motor units (Continued)

in a given image area or a shape of at least one of the confirmed motor units is determined.

20 Claims, 15 Drawing Sheets

(51) Int. Cl.
*A61B 5/00* (2006.01)
*G01R 33/563* (2006.01)

(52) U.S. Cl.
CPC . *G01R 33/56316* (2013.01); *G01R 33/56341* (2013.01); *G06T 2207/10088* (2013.01); *G06T 2207/30004* (2013.01)

(58) Field of Classification Search
CPC ............ A61N 1/36067; A61N 1/36082; A61N 1/36132; A61N 1/0534; G16H 20/40; G06T 7/0016; G06T 2207/10088; G06T 2207/30004; G06T 7/0012; G01R 33/56316; G01R 33/56341
See application file for complete search history.

(56) References Cited

U.S. PATENT DOCUMENTS

| | | | |
|---|---|---|---|
| 10,894,158 B2 * | 1/2021 | Parker | A61N 1/36062 |
| 11,110,270 B2 * | 9/2021 | Parker | A61B 5/377 |
| 11,446,504 B1 * | 9/2022 | Lee | A61N 1/36062 |
| 2002/0135367 A1 | 9/2002 | Ueno et al. | |
| 2008/0004522 A1 * | 1/2008 | Finni | A61B 5/4884 600/415 |
| 2011/0009732 A1 | 1/2011 | Sugiyama et al. | |
| 2015/0257675 A1 * | 9/2015 | Bottomley | G01R 33/56 600/423 |
| 2018/0038932 A1 * | 2/2018 | Arunachalam | G01R 33/56 |
| 2019/0261876 A1 * | 8/2019 | Ghosh | A61B 5/1107 |
| 2019/0261909 A1 * | 8/2019 | Torres | A61B 5/4082 |
| 2020/0054234 A1 * | 2/2020 | Vaara | A61B 5/055 |
| 2020/0069197 A1 * | 3/2020 | Samarage | G16H 50/20 |
| 2021/0106830 A1 * | 4/2021 | Provenza | A61B 5/37 |

OTHER PUBLICATIONS

Brenneck, Michael J. et al. "Mechanical Effects of Genioglossus Muscle Stimulation on the Pharyngeal Airway by MRI in Cats" Respiratory Physiology & Neurobiology, vol. 156; pp. 154-164; 2007.
Schwartz, Martin et al. "Spontaneous Mechanical and Electrical Activities of Human Calf Musculature at Rest Assessed by Repetitive Single-Shot Diffusion-Weighted MRI and Simultaneous Surface Electromyography" Magnetic Resonance in Medicine; vol. 70, No. 5; May 1, 2018.
Steedle, Günter et al. "Addressing Spontaneous Signal Voids in Repetitive Single-Shot DWI of Musculature: Spatial and Temporal Patterns in the Calves of Healthy Volunteers and Consideration of Unintended Muscle Activities as Underlying Mechanism" NMR IN Biomedicine; vol. 28, No. 7; Jul. 1, 2015.
International Search Report for International Application No. PCT/GB2019/051271, dated Aug. 26, 2019.
Written Opinion for International Application No. PCT/GB2019/051271, dated Aug. 26, 2019.
Combined Search and Examination Report Under Sections 7 and 18(3) for Great Britain Application No. 1808950.8, dated Oct. 21, 2019.
Sako, Wataru et al. "The Abnormal Network-Network Interaction in the Brain of Amyotrophic Lateral Sclerosis" (Includes an English Translation of the Abstract) Clinical Neurophysiology; vol. 46; Isue 1; 2018; https://doi.org/10.11422/jscn.46.9.
Whittaker, Roger G. et al. "Functional Magnetic Resonance Imaging of Human Motor Unit Fasciculation in Amyotrophic Lateral Sclerosis" American Neurological Association; vol. 85; No. 3; Mar. 2019.
Notice of Reasons for Refusal (Including Translation) for corresponding Japanese Patent Application No. 2020-566726, dated Jan. 6, 2023.

* cited by examiner

SYSTEM FOR PROCESSING IMAGES TO DETECT PROPERTIES OF SKELETAL MUSCLE

CROSS-REFERENCE TO RELATED APPLICATIONS

This application is a national stage application under 35 U.S.C. 371 of PCT Application No. PCT/GB2019/051271 having an international filing date of 9 May 2019, which designated the United States, which PCT application claimed the benefit of Great Britain Application No. 1808950.8, filed 31 May 2018, each of which are incorporated herein by reference in their entirety.

FIELD OF THE INVENTION

The present invention relates to an apparatus, method and computer program for processing medical magnetic resonance images to detect one or more properties of motor units that control muscular contraction.

BACKGROUND OF THE INVENTION

Nerve and muscle diseases such as, for example, motor neurone disease which is sometimes denoted amyotrophic lateral sclerosis (ALS), which affects nerves in the brain and spinal cord that control voluntary muscles can be difficult to diagnose. For such neurodegenerative diseases, early diagnosis is desirable because early intervention with medical treatment is most effective in delaying progress of the disease. However, currently available tests performed to diagnose nerve and muscle diseases are invasive, time consuming to perform and may have to be repeated a number of times before a diagnosis can be reliably made. A current "gold-standard" test having these drawbacks is electromyography (EMG). EMG involves a medical professional inserting a metal needle through the skin of a patient to penetrate into a muscle. The needle is then used to record electrical activity from a volume of muscle within approximately 1 mm$^3$ of the needle tip. The needle tip is typically moved around inside the muscle for several minutes to increase the accuracy of the reading, which can be painful for a patient. The limitation of only being able to probe electrical activity in such a small muscle volume via the needle tip means that the needle insertion process is typically repeated in up to ten different muscles as part of a process that may last up to an hour, but despite this the volume of muscle sampled is tiny compared to the total muscle volume. The repetition in the different muscles can reduce the likelihood of false positive diagnoses. Due mainly to the problem of sparse sampling of the muscles, the EMG technique has a sensitivity of less than 50% in certain neuromuscular diseases. At present, a small but significant portion of patients (around 10%) die of motor neurone disease without even having been positively diagnosed with the disease. Thus there is a need for a more accurate and less invasive technique for detecting muscular abnormalities such as those associated with neuromuscular diseases prior to making a diagnosis.

BRIEF SUMMARY OF THE DISCLOSURE

According to a first aspect, the present invention provides machine readable instructions stored on a machine readable medium, the machine readable instructions upon execution to cause processing circuitry to:

receive a time series of Magnetic Resonance, MR, images representing a slice of a body part;

analyze the time series of images to identify one or more signal voids in one or more images of the series, a signal void being a localized region of signal attenuation;

correlate the identified signal voids with candidate motor units of skeletal muscle, wherein the correlation comprises performing a comparison of at least one characteristic of the identified signal voids in the images with a control data set of MR images produced by applying a controlled stimulus to a motor nerve in control subjects to establish inherent characteristics of signal voids corresponding to motor units of skeletal muscle; and analyze properties of candidate motor units validated via the comparison as confirmed motor units and determine at least one of: a firing frequency of at least one of the confirmed motor units, a size of at least one of the confirmed motor units, a number of confirmed motor units in a given image area or a shape of at least one of the confirmed motor units.

According to a second aspect, the present invention provides a data processing apparatus having one or more processors comprising:

circuitry to receive a time series of Magnetic Resonance, MR, images representing a slice of a body part;

circuitry to analyze the time series of images to identify one or more signal voids in one or more images of the series, a signal void being a localized region of signal attenuation;

circuitry to correlate the identified signal voids with candidate motor units of skeletal muscle, wherein the correlation comprises performing a comparison of at least one characteristic of the identified signal voids in the images with a control data set of MR images characterizing inherent properties of signal voids corresponding to motor units of skeletal muscle; and circuitry to analyze properties of candidate motor units validated via the comparison as confirmed motor units and determine at least one of: a firing frequency of at least one of the confirmed motor units, a size of at least one of the confirmed motor units, a number of confirmed motor units in a given image area or a shape of at least one of the confirmed motor units.

According to a third aspect, the present invention provides a method of processing images to determine one or more properties of skeletal muscle, the method comprising:

receiving a time series of Magnetic Resonance, MR, images representing a slice of a body part;

analyzing the time series of images to identify one or more signal voids in one or more images of the series, a signal void being a localized region of signal attenuation;

correlating the identified signal voids with candidate motor units of skeletal muscle, wherein the correlation comprises performing a comparison of at least one characteristic of the identified signal voids in the images with a control data set of MR images to validate at least a subset of the candidate motor units as confirmed motor units; and analyzing properties of the confirmed motor units to determine at least one of: a firing frequency of at least one of the confirmed motor units, a size of at least one of the confirmed motor units, a number of confirmed motor units in a given image area or a shape of at least one of the confirmed motor units.

Other aspects and features of embodiments of the invention are provided in the appended claims.

BRIEF DESCRIPTION OF THE DRAWINGS

Embodiments of the invention are further described hereinafter with reference to the accompanying drawings, in which.

DETAILED DESCRIPTION

Figure 1:
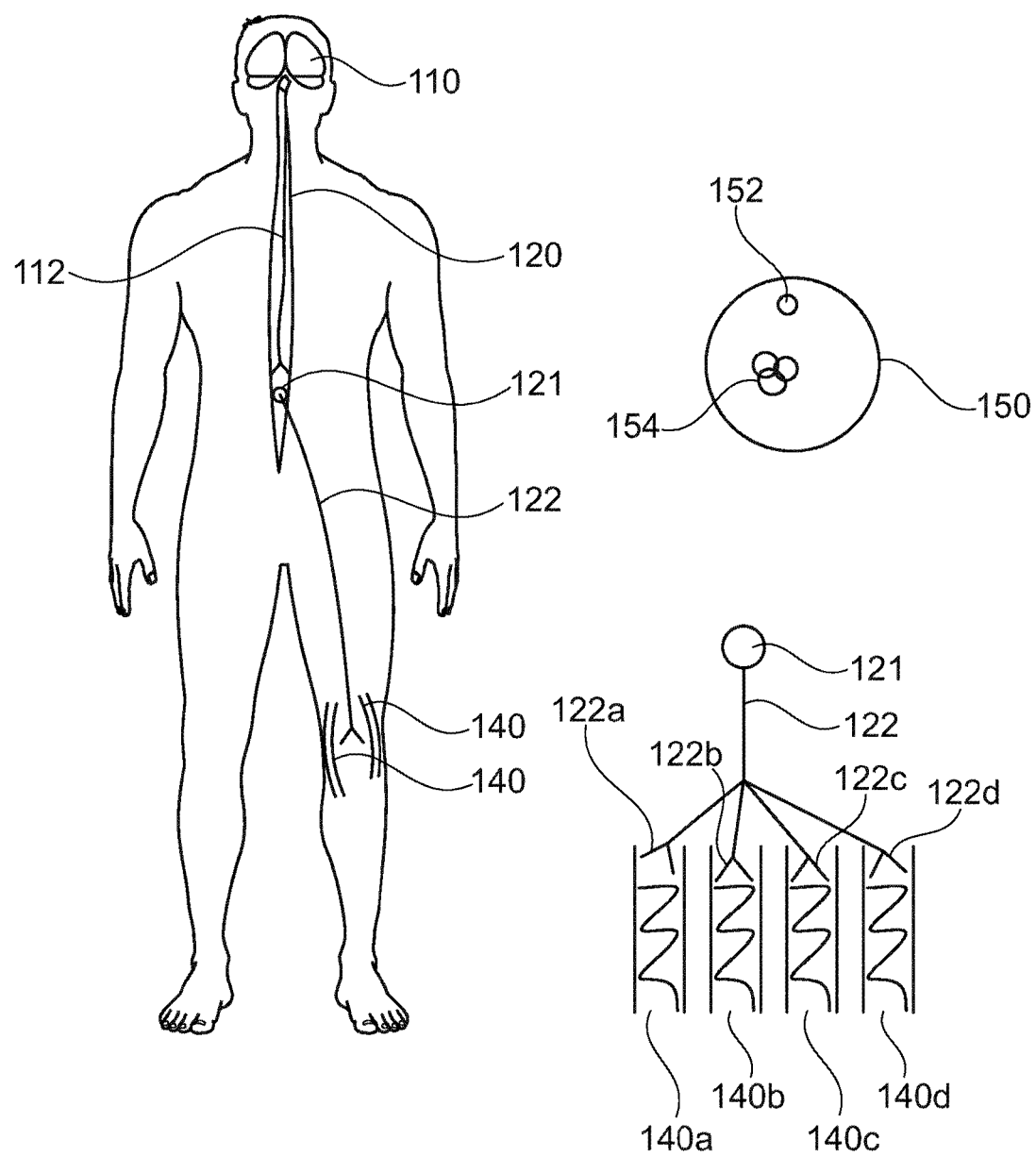
FIG. 1 schematically illustrates motor neurones and motor units that control contraction of voluntary muscles.

FIG. 1 schematically illustrates motor neurones and motor units that control contraction of voluntary muscles. FIG. 1 shows a brain 110 in which an upper motor neuron 112 is located either in a motor region of the cerebral cortex or in the brain stem and a spinal cord 120 into which the upper motor neuron 112 sends electrical impulses to a lower motor neuron 122 within the spinal cord. The upper motor neuron descends into the spinal cord 120 to the level of an appropriate spinal nerve root, where it synapses with the lower motor neuron 122. The lower motor neuron 122 has a soma 121 in the spinal cord, an axon 130 and a plurality of axon terminals. Each axon terminal innervates a fibre (or muscle cell) of skeletal muscle to control contraction of the muscle fibres. A single lower motor neuron 121, 122 and all of the skeletal muscle cells (or fibres) 140a, 140b, 140c, 140d innervated by that lower motor neuron's plural axonal terminals 122a, 122b, 122c, 122d is denoted a "motor unit". Larger muscles such as leg muscles have larger motor units to simultaneously contract hundreds of muscle cells (up to 1000) whereas smaller muscles such as finger muscles, which provide finer control have smaller motor units with fewer axonal terminals and controlling perhaps as few as five muscle cells. All skeletal muscle cells of a single motor unit will tend to contract together. Groups of motor units may work together to contract a single muscle such as a muscle of one of the limbs or trunk. A cross section 150 of a muscle shows a plurality of muscle fibres 152, 154. controlled by a respective plurality of motor units. There may be several hundred different motor units controlling contraction of a single muscle.

In patients affected by motor neurone disease, the lower motor neurons 121, 122 progressively die resulting in progressive loss of entire motor units because the muscle cells tend to atrophy when the corresponding lower motor neuron dies. However, before a motor neuron fails completely it tends to start to fire spontaneously resulting in involuntary muscle twitches denoted "fasciculations". A fasciculation may result from a single motor unit firing. When individual motor units fail neighbouring motor units tend to extend their axon terminals into the area of muscle previously controlled by the failed motor unit. As a result, the size of the remaining motor units tends to increase. Furthermore, when a muscle is depleted of some motor units the remaining motor units tend to increase their firing frequency to achieve contraction of the muscle, compensating for the absence of the failed motor units. Thus some example characteristics of motor neurons disease that may be apparent from properties of motor units are at least one of: (i) a reduced number of motor units in a given area of muscle; (ii) an increased size of a subset of motor units relative to a size of motor units in a healthy muscle; (iii) an increased rate of firing of motor units as a result of fasciculations. A typical firing rate of a motor unit in a healthy muscle may be 5-15 Hz and a typical diameter of muscle cells of a motor unit may be in a range 1-10 mm, although these numbers are non-limiting examples.

Sparse and spontaneous events such as the involuntary motor unit firing associated with fasciculations can be extremely challenging to study in a systematic way. Although motor unit numbers may be estimated using EMG or by stimulation of muscles using electrical pulses, both of these known techniques can be painful, have lower than desirable diagnostic accuracy and require patient co-operation making them different to perform in children or in the elderly. According to the present technique MRI images may be processed to determine motor unit activity that may be indicative of a neuromuscular disease.

In some embodiments, diffusion weighted imaging (DWI) may be used. DWI is a variant of MRI often used to map white matter in the brain to assess axonal integrity and to map white matter tracts. It has been noted that when DWI is used to examine tissue microstructure in skeletal muscle, spontaneous and relatively brief (for example, hundreds of milliseconds) signal voids appear in the captured images. Although these signal voids were expected to be associated with some kind of muscle activity, it was unclear exactly why these signal voids appeared. However, according to the present technique, control data has been produced demonstrating that the signal voids can be specifically mapped to firing of individual motor units.

Figure 2A:
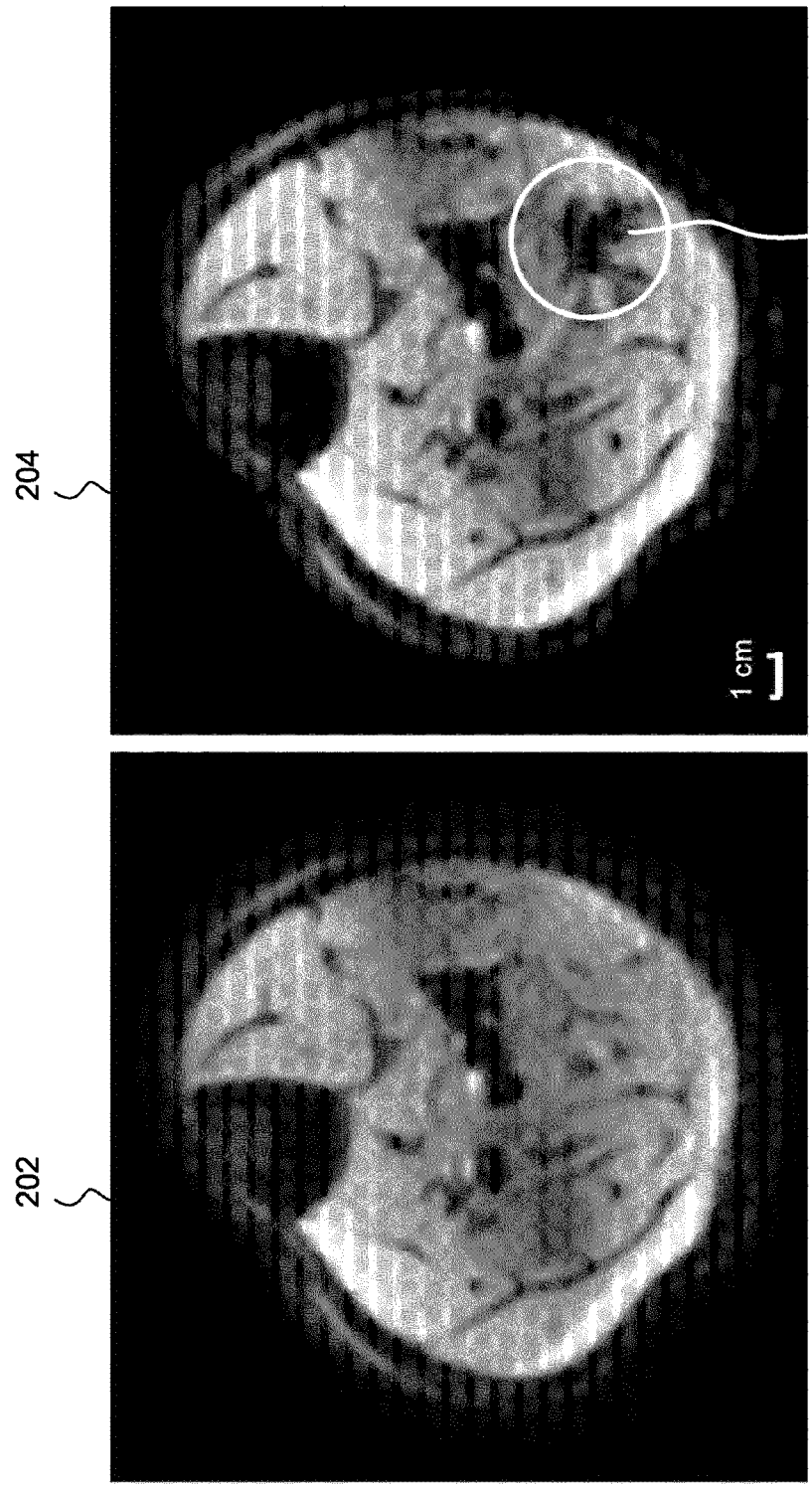
FIG. 2a schematically illustrates a pair of Magnetic Resonance (MR) images of a leg muscle showing an appearance of spontaneous signal voids.

FIG. 2a schematically illustrates a pair of diffusion weighted MRI images of a leg muscle showing an appearance of spontaneous signal voids. A first MRI image 202 shows features of a leg muscle at a first scan time and a second MRI image 204 shows the same leg muscle captured 3 seconds later. A comparison of the two images reveals that there is an area 206 of signal attenuation in the second image 204 that was not present in the first image 202. The area 206 of signal attenuation is a signal void associated with a single motor unit firing. The signal void is a transient feature of the image.

Figure 2B:
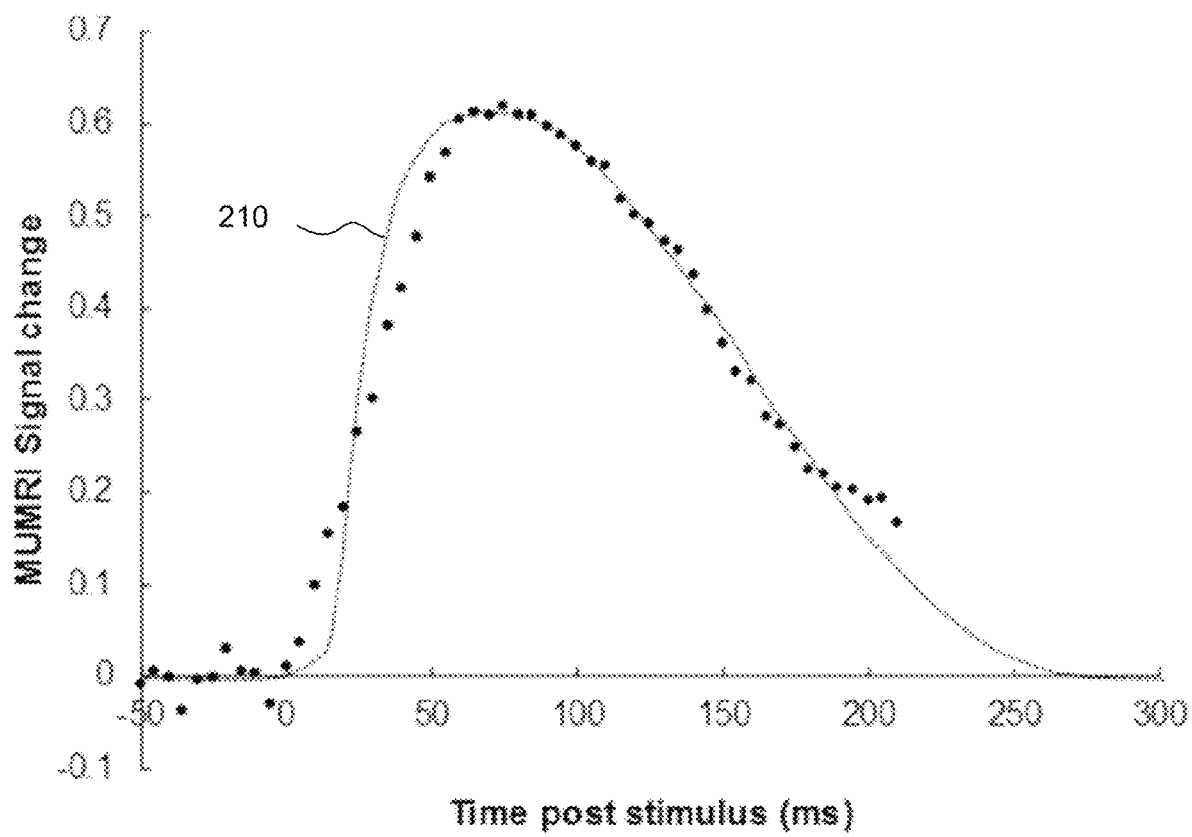
FIG. 2b schematically illustrates a graph of MR signal change against time from application of an external electrical stimulus to a muscle showing a stimulation response temporal profile of the muscle.
Figure 3A:
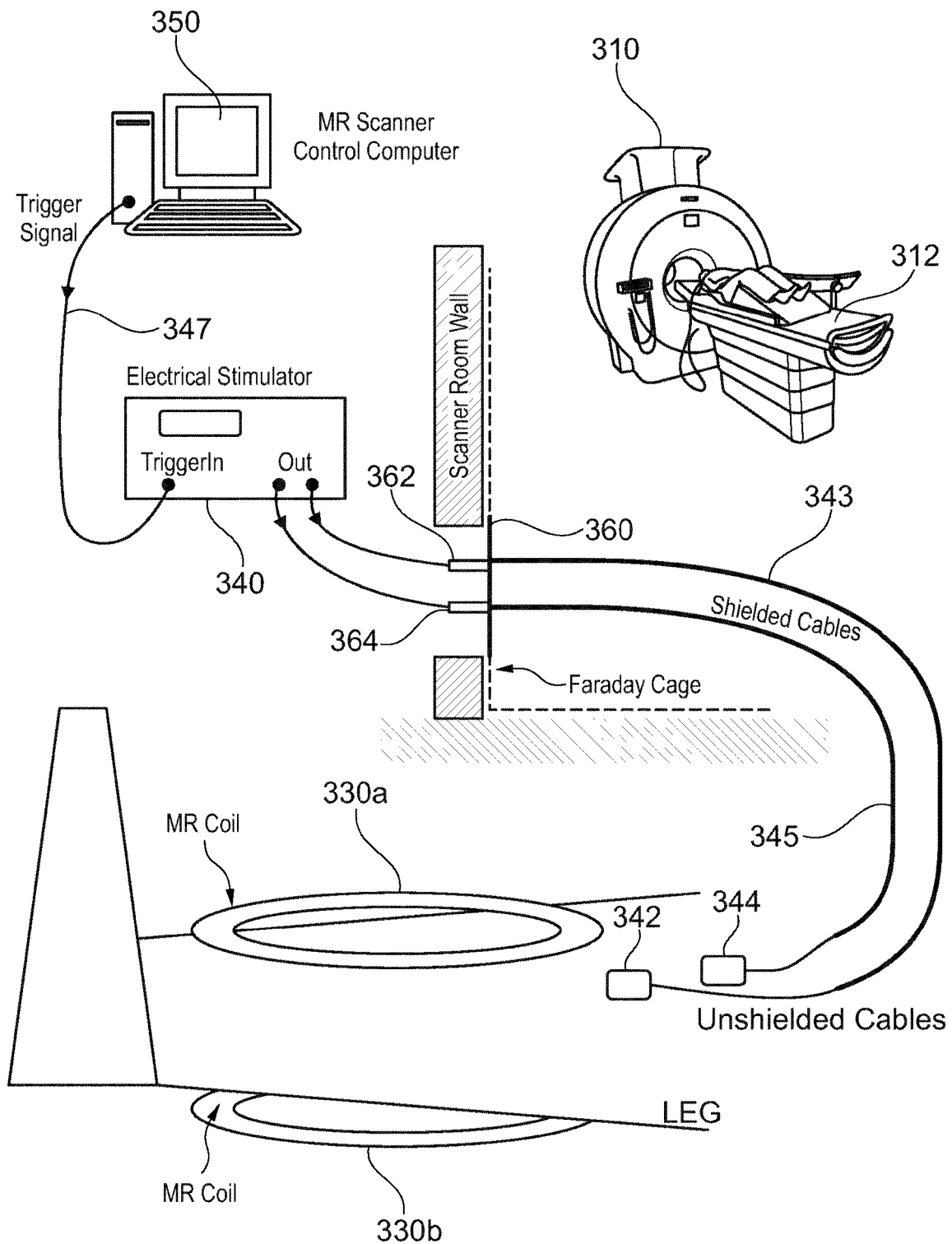
FIG. 3a schematically illustrates an apparatus arrangement for performing MRI imaging to collect control data to discriminate between MRI signal voids associated with motor unit activity and MRI signal voids unlikely to be associated with motor unit activity.

FIG. 2b schematically illustrates a graph of DWI MRI signal change against a time from application of an external electrical stimulus to a tibialis anterior muscle, showing a stimulation response temporal profile of the muscle. The tibialis anterior muscle is located near the shin on the lower leg. A single external electrical stimulus current was applied to the peroneal nerve of a patient for a short duration (for example, 0.3 milliseconds) and the stimulus was removed at time zero on the graph of FIG. 2b. A change in the signal level relative to a mean value before the external stimulus was applied is plotted against the time post stimulus in milliseconds. This graph relates to a region od interest comprising a plurality of pixels. Single pixels are expected to show the same behaviour but noise would be more apparent. The empirical data (dots) corresponding to the signal change magnitude in the analysed MR images as a function of post stimulus time is plotted alongside a curve 210 that is based on medical literature data (Neuroscience, "The Motor Unit", D Purves et al, 2001) illustrating how force generation in a motor unit is expected to vary with time. It can be seen that the empirical data agree well with the theoretical motor unit response curve. The peak signal change responsive to the electrical stimulation is at around 75 ms and the response curve profile spans from 0 to around 250 ms post-stimulus. FIG. 3a schematically illustrates an apparatus arrangement for performing MR imaging to collect control data to discriminate between MRI signal voids associated with motor unit activity and MRI signal voids unlikely to be associated with motor unit activity. The apparatus comprises a MRI machine 310 having a patent table 312, a leg holder 320 to keep a patient's leg in a fixed position during a scanning process (shown in FIG. 3b and FIG. 3c), a pair of flexible coils 330a, 330b to be placed one above and one below a patient's leg during an MRI scan image capture, a bipolar (electrical) stimulator 340 to generate a controlled electrical current to stimulate a patient's muscle via a pair of electrodes 342, 344 and associated connecting wires 343, 345. The connecting wires between the bipolar stimulator 340 and the electrode pair 342, 344 each have a shielded portion corresponding to a length of cable inside the scanner room. The scanner room wall acts as a Faraday cage to block electromagnetic fields. This prevents external RF (radio frequency) signals from being added to data collected from the patient, which could affect the resulting captured image. A filter plate 360 is provided on an interior of the scanner room wall and each of the two connecting cables 343, 345 is provided with a low pass filter 362, 364 just external to the scanner room wall. The low pass filters prevent pickup form activity of the scanner from affecting the stimulus.

The bipolar stimulator 340 may be connected via a wired or wireless connection to a scanner controller 350. The scanner controller 350 and the electrical stimulator are located outside the scanner room in the FIG. 3a example. The scanner controller 350 has at least one processor to execute software to control the MRI scanner 310 to control timing of MRI image capture and to set scanner parameters. The processing circuitry of the scanner controller may comprise general purpose or special purpose processing circuitry, a graphics processing unit, an image processing unit or the like. A trigger signal 347 may be sent from the scanner controller 350 to the bipolar stimulator 340 to trigger generation of a given electrical stimulus signal to the electrode pair 342, 344. The connection between the scanner controller 350 and the bipolar stimulator 340 enables coordination of a timing of an application of an electrical stimulus to a motor nerve of a patient via the pair of electrodes 342, 344 and timing of initiation of capture of a time series of MRI images. For example, the scanner controller 350 may control the MRI scanner 310 to initiate image capture of the first image of a time series of image such that it a response of motor units of skeletal muscle is most likely to be captured within the time series. For example, referring to FIG. 2b, where the expected motor unit response extends from a time approximately coinciding with application of the electrical stimulus, peaking at between around 50 ms to 100 ms post-stimulus and fading away at around 250 ms post stimulus. The MRI signal change as a function of time may have different characteristic curves depending on which particular nerve is stimulated and is not limited to the signal change profile illustrated in FIG. 2b. In some examples, the scanner controller 350 may control capture of a plurality of scan images within the 250 ms expected motor unit response period. In other examples, it may be sufficient to capture a single MRI image to coincide or to approximately coincide with the 50-150 ms peak response region and to capture successive images of the time series after the motor unit response to the first electrical stimulus has subsided. Diffusion-weighted imaging (DWI) is a form of magnetic resonance imaging based on measuring Brownian (i.e. random) motion of water molecules within a voxel of tissue, where a voxel is a volumetric pixel having three dimensions rather than two. Diffusion of water inside a container is effectively free diffusion whereas in tissues of a living human or animal body, water molecule diffusion may be inhibited, for example, by cell membrane boundaries, by cellular swelling or by highly cellular tissues for example. Thus DWI can be used to discriminate between healthy tissue and a tumour or may be used to map white matter (neural tracts) in the brain. According to the present technique, DWI may be used to discriminate between a contracting muscle fibre or cell and a relaxed muscle fibre. In this case the DWI detects the change in water position within the voxel due to the fibre contraction, instead of due to Brownian motion. The MRI scan method is a DWI method, but according to the present technique, rather than measuring diffusion, the sequence is sensitive to any effect which changes the relative location of water molecules within a voxel during the sensitive time period of the DWI scan. Normally this would be due to Brownian motion of the water molecules, but according to the present technique, contractions or relaxations of the muscle "squeeze" or "stretch" the distribution of water molecules within the tissue. This mechanism has ben recognised and utilised.

As one alternative to DWI imaging, phase contrast MRI (PC-MRI) may be used to capture a time series of images to detect muscle fibre contractions associated with the firing of motor units. PC-MRI may be used to determine flow velocities and can provide four-dimensional imaging to include three spatial dimensions plus time. This allows changes in a time series of captured images to be determined to discriminate between times when muscle fibres in an image area are contracting and times when the same muscle fibres are not contracting. The imaging parameters may be adjusted to increase the likelihood of detecting the muscle fibre contractions. Signal voids may be detected in PC-MRI images. For DWI a "b value" is an imaging parameter that may be adjusted. Application of a gradient pulse (gradient magnetic field) induces a phase shift in the precession of protons and applying a gradient and then reversing it exactly means that particles that have moved end up with a phase shift whereas particles that have not moved experience no net phase shift. An MR signal from a region of a body such as a muscle region depends on phase coherence of spins (water molecules) in the region. A drop in magnitude of an MR signal from a certain body region due to application of two equal and opposite gradient pulses indicates that there is a change in the water distribution in the region concerned, which can be due to diffusion and muscle contraction or relaxation. DWI pulse sequences may consist of two gradient pulses of magnitude G, duration d and time interval A. The amount of MR signal loss may depend on:

(i) a rate of diffusion or tissue contraction in that body region
(ii) the magnitude G of the gradient magnetic fields
(iii) the duration d for which the gradient magnetic fields are applied in each direction
(iv) the time interval A between the gradient magnetic fields By adjusting the duration, spacing and strength of diffusion gradients, a DWI image can be made more or less sensitive to molecular motion such as motion of water molecules. A higher b value means that the gradient pulses are either applied for longer or their magnitude is higher. Both of these conditions is likely to lead to a higher MR signal loss for a given rate of diffusion in a region in the body. According to the present technique b values in a range of between 10 and 50 seconds per $mm^2$ were found to provide a rate of signal loss that allowed muscle contractions associated with firing of motor units to be readily distinguished from non-contracting muscle regions. When looking for an electrically stimulated response 10 to 50 seconds per $mm^2$ is a good range but when looking for spontaneous fasciculations in disease e.g. ALS) it has been found that 100 to 200 seconds per $mm^2$ is a good range in which to operate. However, the distinction between contracting muscle fibres and non-contracting muscle fibres may also be readily established at other b values or by using other MRI techniques such as phase contrast MRI. Signal voids associated with a higher level of signal attenuation of MR image pixels may be associated with volitional muscle contraction, externally stimulated muscle contraction or involuntary muscle contractions such as fasciculations.

Using the apparatus arrangement of FIG. 3, a set of control data may be collected for one or more control subjects by externally stimulating a nerve such as the peroneal nerve to stimulate contractions in muscle fibres of the tibialis anterior in the shin region of the lower leg. A time series of images may be captured at a predetermined timing relative to application of the electrical stimulus by the bipolar stimulator 340. The captured time series of images and known times of electrical stimulation may be used to detect and identify characteristics of the images associated with muscle contraction. The time series image capture may be performed for a plurality of different b values and for one or more levels of electrical stimulation (e.g. different currents).

Figure 3B:
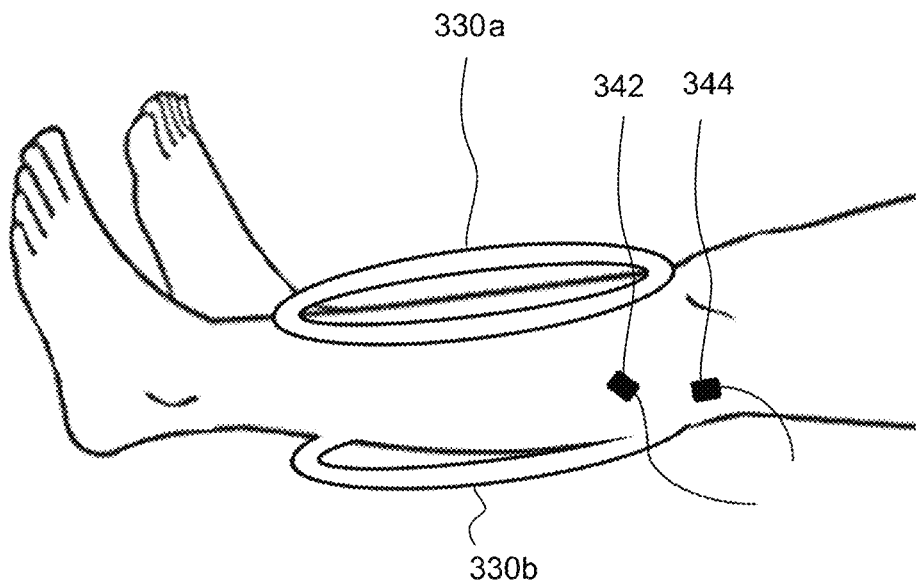
FIG. 3b schematically illustrates a first view of a patient's leg showing two flexible coils and a pair of electrodes to deliver external electrical stimulation.
Figure 3C:
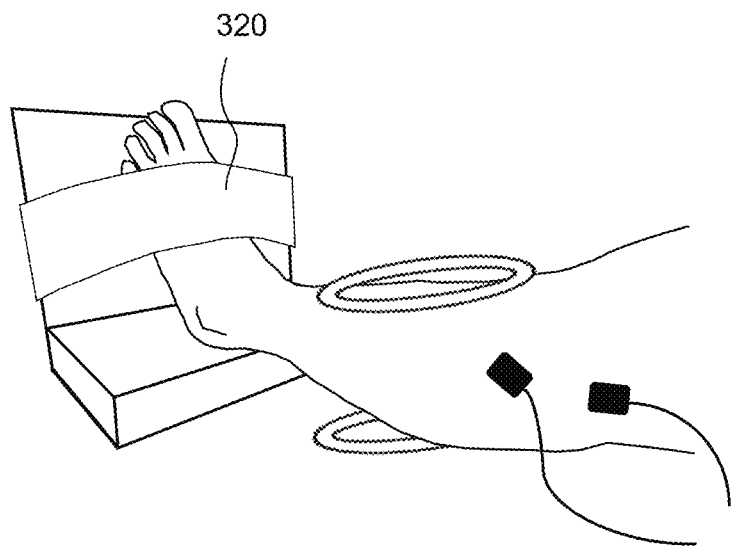
FIG. 3c schematically illustrates a second view of a patient's leg showing a leg holder, a pair of flexible coils and a pair of electrodes to deliver external electrical stimulation.

The bipolar stimulator 340 may be, for example, a Digitimer DS5 programmable electrical stimulator adapted for in-bore scanning using extended cables 343, 345 and low-pass filters 362, 364 at a Faraday cage and the MR compatible electrodes 342, 344 which in this example were shielded (portions inside the scanner room as shown in FIG. 3a) except for the final 15 cm closest to the electrodes, at which point the cables are closely spaced to minimize or at least reduce pickup. The bipolar stimulator 340 is interfaced to the scanner via the scanner controller 350 for synchronization of image acquisition and muscle contraction inducing stimulation. A pair of electrodes such as 15×20 mm electrodes may be placed 2 cm apart at the fibular head for stimulation of the left common peroneal nerve to the tibialis anterior (TA) using a 0.3 mS mono-polar pulse. Placement of the electrodes on the leg of a subject is shown in FIGS. 3b and 3c. The subject's leg may be positioned in the holder 320 including a foot rest to which the foot may be immobilized, in the MRI scanner 310 and the pair of flexible surface coils 330a, 330b may be positioned to each side or above and below the leg. The flexible surface coils 330a, 330b may be, for example, 10 cm elliptical coils.

FIG. 3b schematically illustrates a first view of a patient's leg showing two flexible coils 330a, 330b and a pair of electrodes 342, 344 to deliver external electrical stimulation.

FIG. 3c schematically illustrates a second view of a patient's leg showing the leg holder 320, the pair of flexible coils 330a, 330b and the pair of electrodes 342, 344 to deliver external electrical stimulation.

Example control data collection results have been obtained by performing MRI scans of six healthy volunteers using an axially oriented diffusion weighted spin echo echo planar imaging (SE-EPI) sequence with sensitization in the through slice direction, along a main muscle fibre axis (1.5×1.5 mm resolution, 10 mm slice, repetition time (TR)/ echo time (TE)=1000/36 ms, pulse gradient duration=7 ms). A diffusion weighted scan was first collected shifting the acquisition time relative to the stimulus at various b-values (0-100 s·$mm^{-2}$) to map the peak signal response in two subjects. A scan series of sixty images were then collected at peak response time with b-values of 0 (control), 10 and 20 s·$mm^{-2}$ and with current incrementing in 0.04 mA per acquisition. As the external stimulation current increases, threshold stimulation currents for successive motor units are reached causing a new motor unit to fire at each threshold current and expanding an area of muscle involvement participating in muscle contraction of muscle fibres associated with the particular muscle cells. In this example control data collection the scans were repeated twice for reproducibility.

Regions of interest and pixelwise analysis of one or more images of a time series of MRI images was performed to assess the signal response as a function of b value and the effects of incrementing external current on muscle involvement.

Figure 4A:
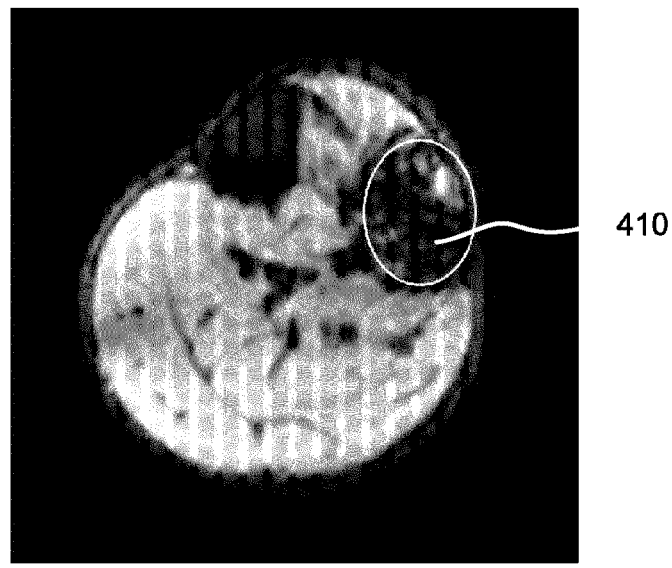
FIG. 4a is an MRI image schematically illustrating signal voids at a time of peak signal change responsive to an external electrical stimulus.

FIG. 4a shows an example time course of signal change relative to the stimulus for different b values, together with the image at peak signal change (b=50 s·mm$^{-2}$). Signal attenuation is seen associated with contraction of the muscle fibres during the diffusion sensitive period of the scan ($\Delta$). Differences in attenuation are seen between b-values of 1 and 20 s·mm$^{-2}$, but which plateau for be values above 50 s·mm$^{-2}$. A line 412 corresponds to a b value of 1 s·mm$^{-2}$. A line 414 corresponds to a b value of 10 s·mm$^{-2}$. A line 416 corresponds to a b value of 20 s·mm$^{-2}$. A line 418 corresponds to a b value of 50 s·mm$^{-2}$ and a line 420 corresponds to a b value of 100 s·mm$^{-2}$.

Figure 4B:
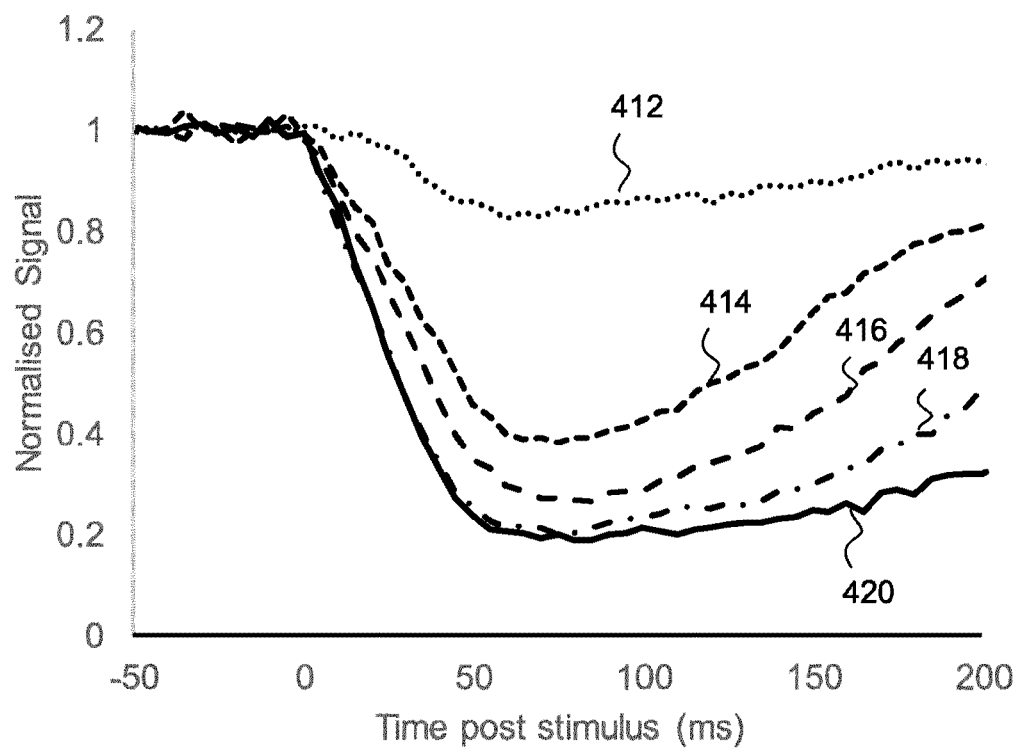
FIG. 4b schematically illustrates an example of a time course of MR signal change relative to external electrical stimulus at different diffusion b values.
Figure 5:
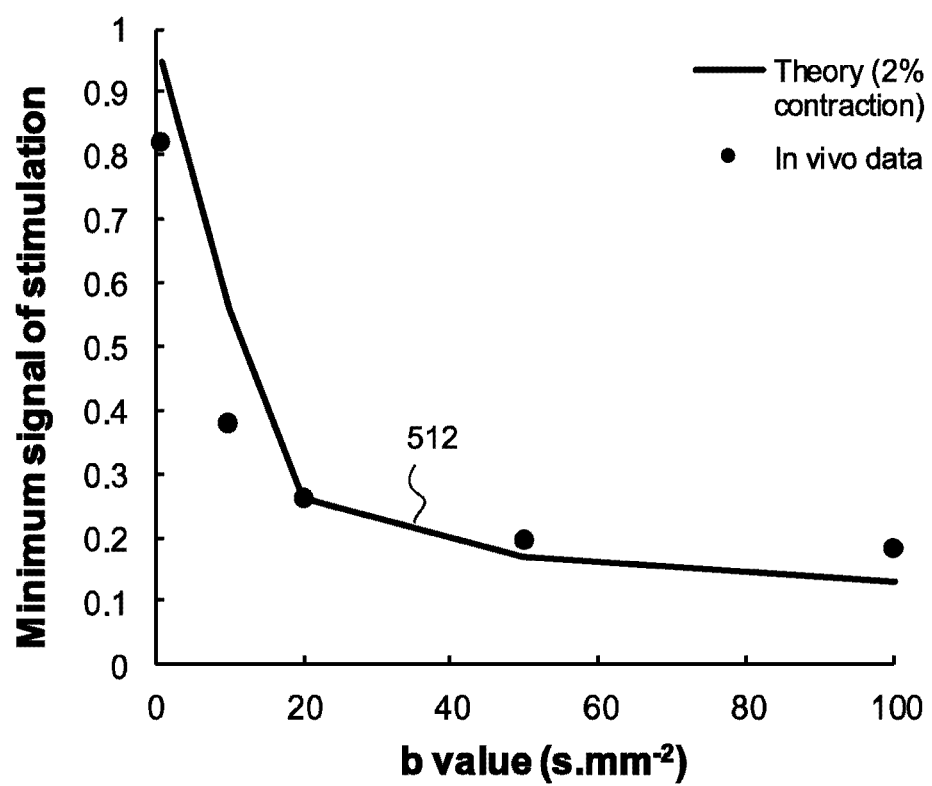
FIG. 5 schematically illustrates peak MR signal attenuation derived from the data of FIG. 4b.

FIG. 5 schematically illustrates peak MR signal attenuation derived from the data of FIG. 4b. The data points plotted are in vivo data, which is plotted together with a line 512 representing theoretical results assuming a 2% (200 µm) linear contraction of the muscle fibres. The results show a good agreement between theoretical predictions and empirical data confirming the hypothesis that signal voids in MR images are associated with individual motor units firing and associated muscle fibre contractions.

Figure 6:
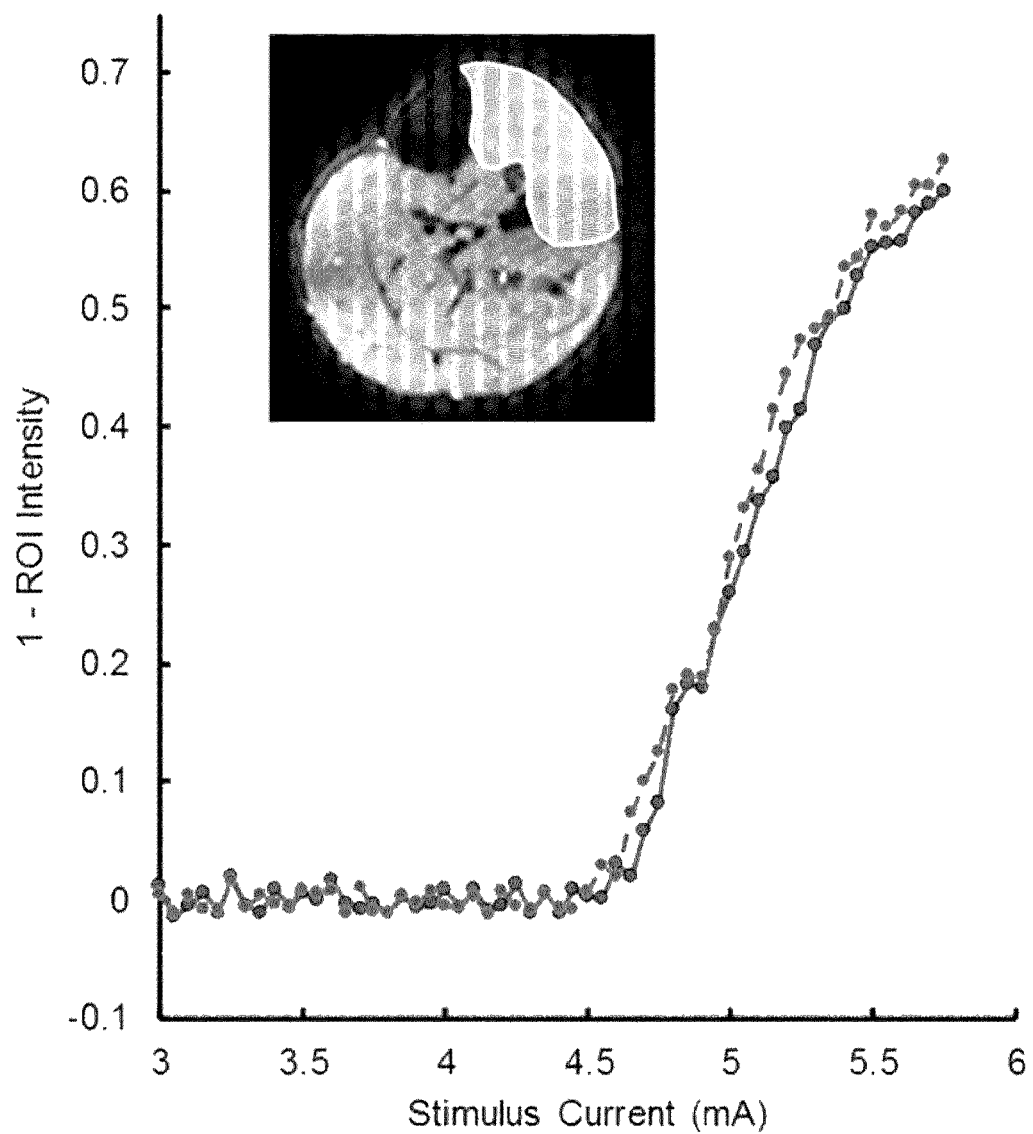
FIG. 6 schematically illustrates an MR image in which an externally electrically stimulated muscle cross section is highlighted and a graph of one minus a mean region of interest (ROI) signal intensity in arbitrary units against stimulus current in mA for the stimulated muscle cross section of the FIG. 6 scan image.

FIG. 6 schematically illustrates activation of different motor units of a muscle region with stimulus current. As each motor unit reaches a threshold current for activation the area of the MR signal changes (signal voids) expands to engulf more pixels in the captured MRI image and a total signal within the whole muscle falls. The graph of FIG. 6 is a plot of 1 minus the mean region of interest (ROI) signal intensity in normalised units on the y-axis against stimulus current in mA on the x-axis. The (1-ROI intensity) is substantially constant for stimulus current values in the range from around 3 mA to just below 5 mA, but increases sharply from a value of zero at 4.5 mA up to a value of about 0.6 at a stimulation current of about 5.5 mA. The sharp decrease in ROI intensity (corresponding to a sharp increase in 1-ROI intensity) is due to the comparatively large number of signal voids associated with motor unit activation and muscle contractions, which appear when a stimulus current is at or above a motor unit activation threshold. The dotted line and the solid line in the FIG. 6 graph represent two distinct measurements, which illustrates a reproducible response to electrical stimulation whereby there is a minimum stimulus current threshold. This is the MRI equivalent of motor unit number estimation in electromyography, but the MRI method according to the present technique is less invasive, faster to implement and can probe more muscle regions with comparative ease.

Figure 7:
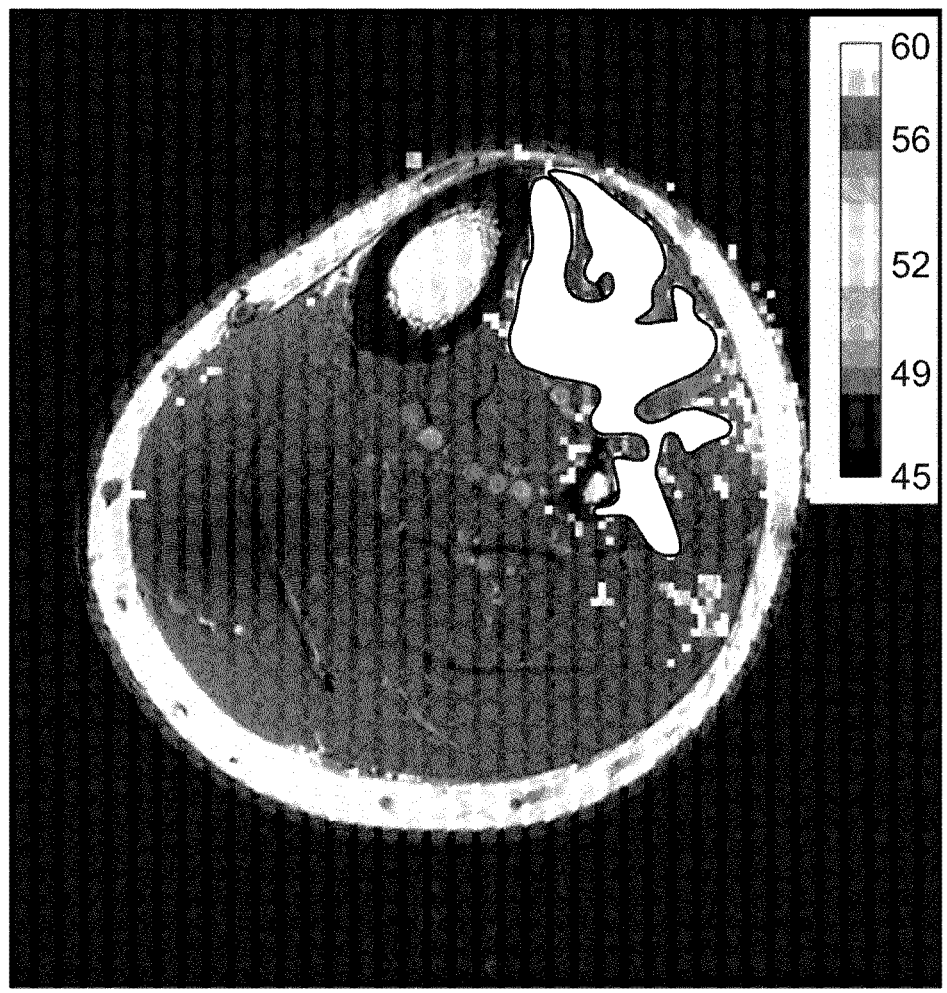
FIG. 7 is an MR image schematically illustrating an example control data set showing a spatial pattern of motor unit firing detected using diffusion weighted imaging with graded electrical stimulation overlaid onto an equivalent T1w-TSE (T1 weighted turbo spin echo) anatomical image.

FIG. 7 is an MRI image schematically illustrating an example control data set showing a spatial pattern of motor unit firing detected using diffusion weighted imaging with graded electrical stimulation overlaid onto an equivalent T1w-TSE (T1 weighted turbo spin echo) anatomical image. The MRI image shown in FIG. 7 is an example of the spatial pattern of the motor unit recruitment with the colour coding indicating the image volume at which the MR signal value corresponding to that pixel fell below three standard deviations of the pre-stimulus signal, which was a test used in this example to categorise pixels of the image as pixels belonging to a signal void.

Figure 8:
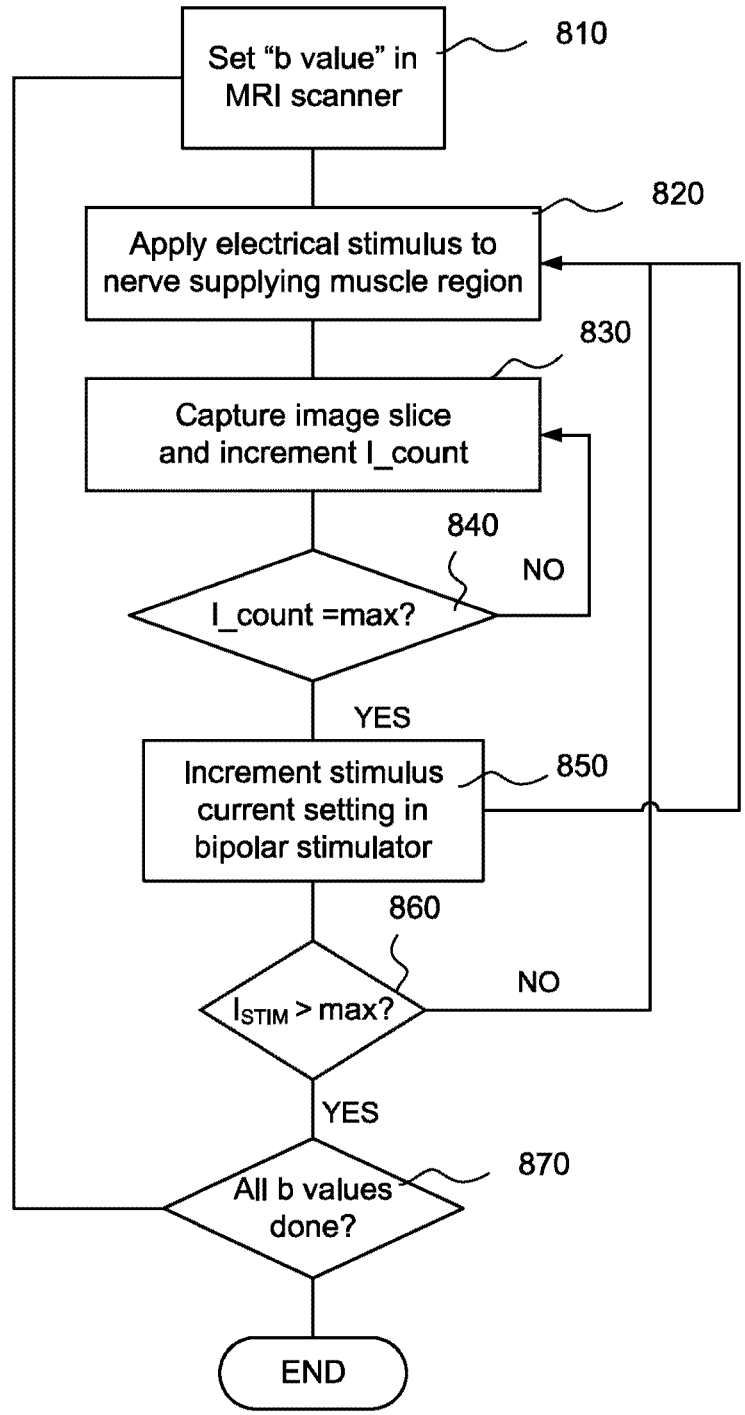
FIG. 8 is a flow chart that schematically illustrates a process for generating a control data set to determine inherent characteristics of MRI signal voids associated with motor unit activity.

FIG. 8 is a flow chart that schematically illustrates a process for generating a control data set to determine inherent characteristics of MRI signal voids associated with motor unit activity. In this example, the time series of images collected are DWI images. The process begins at 810 by setting an initial b value in the MRI scanner. Next, at process element 820 an external electrical stimulus is applied to a nerve of a human subject that supplies a muscle region of interest to trigger muscle fibre contraction in that muscle region. Then at process elements 830 and 840, a predetermined time delay after the electrical stimulation pulse has been applied, a time series comprising a plurality of images is captured to detect signal voids associated with muscle fibre contractions triggered by the stimulus.

At process element 830 a single image is captured in time to coincide with the peak signal change. As shown in the graph of FIG. 2b, the peak signal change may occur between 0 and 150 ms post stimulus. In some embodiments capture of the time series of images may begin before the electrical stimulus is applied, for example around 50 ms before the stimulus is applied, so that a difference between the pre-stimulus signal level and the post-stimulus signal level can be identified when the captured images are processed. Once the time series image capture has been initially triggered at process element 830, which includes initialisation of an image counter I-count, the process proceeds to process element 840 where it is determined whether or not I-count has reach a maximum value corresponding to a full set of time series images. The maximum number of images in a time series is a programmable parameter configurable by a user. If the maximum number of images has not yet been captured then the process returns to process element 830 to capture a further image and to increment I_count, although in some examples I_count=1 with a single image at the peak. When the maximum number of images has been captured, the process proceeds from process element 840 to process element 850. The determination of signal voids may be performed offline, after all of the images have been captured or processing of the time series of captured images may alternatively be performed at least in part in parallel with the MR image capture.

At process element 850, the electrical stimulus current is incremented to a higher value by adjusting a setting of the bipolar stimulator 850 and then the loop of capturing a time series of images, involving process elements 820, 830 and 840 is repeated for the new electrical stimulation current. Progressively increasing the external electrical stimulation current by increments may cause step-wise activation of individual ones of a group of motor units controlling contraction of the muscle region of interest and thus may result in progressively greater MR signal change in captured images as more signal voids appear, reflecting activation of the motor units and resulting in muscle fibre contractions.

At process element 860, after each image time series has been captured for a given stimulation current, it is determined whether or not the maximum stimulation current has been reached and, if so, the MRI scanner b-value may be incremented at process element 870 in an outer loop over b-values. However, if the maximum stimulation current has not yet been reached an inner loop over stimulation current values comprising elements 820, 830, 840 and 850 is completed.

At process element 870, it is determined whether or not all b-values required by a user as part of control data capture have been implemented. If not, the process flow goes back to process element 810, where the b value is set. There may be a predetermined set of b values to be used to collect control data, such as for example b=1, 10, 20, 50, 100 s·mm$^{-2}$ as shown in FIG. 4 described above. It has been found that b values in the range between 10 and 50 s·mm$^{-2}$ provide a good clear distinction between activated motor units and non-activated motor units in an imaged muscle region, but b values outside this range may alternatively be used. If the full range of b-values have been explored at process element 870 then the process ends.

Figure 9:
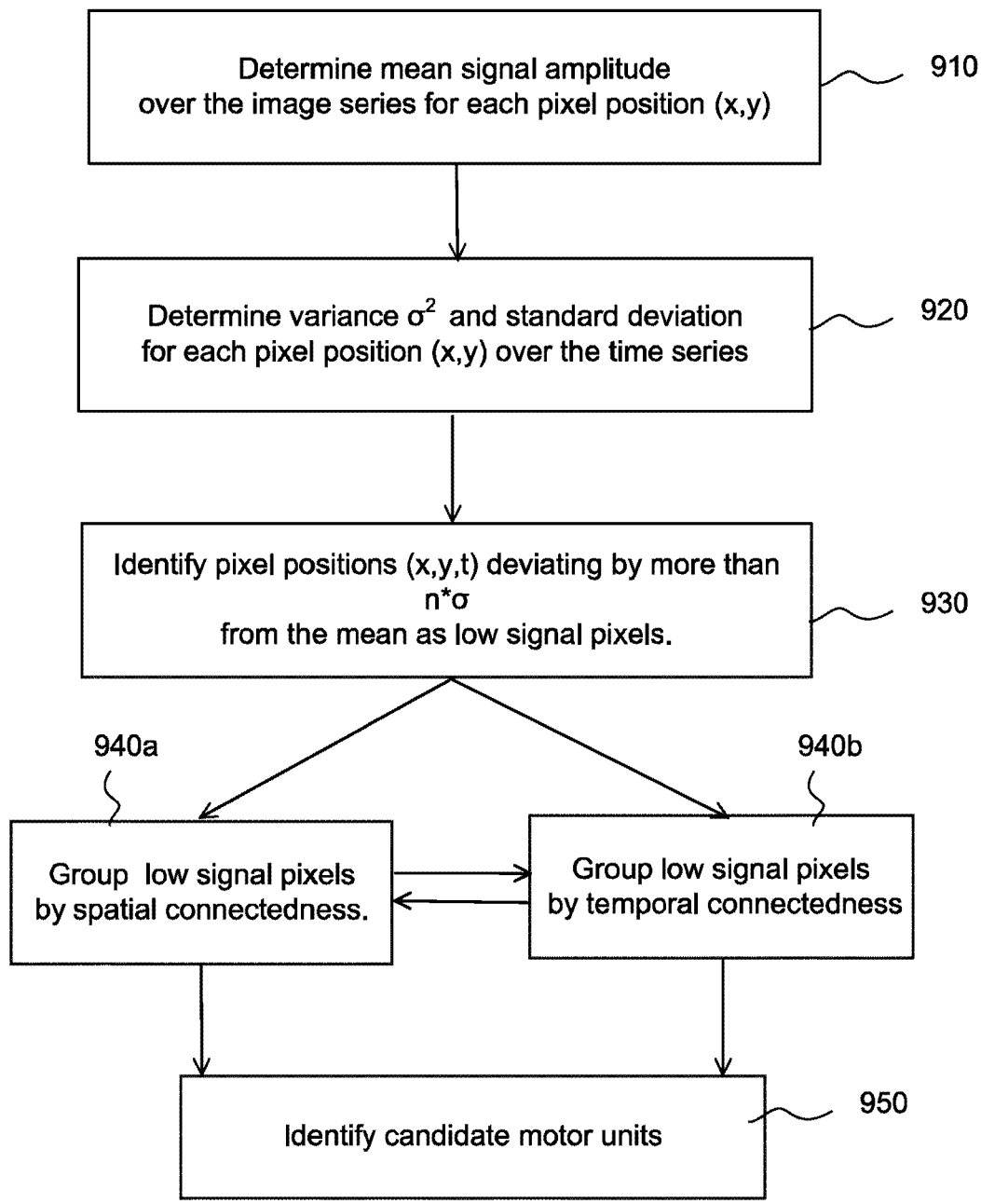
FIG. 9 is a flow chart schematically illustrating processing performed on MRI images of a time series to identify signal voids potentially associated with motor unit activity.

Although in the flow chart of FIG. 9 the control data set is generated using external electrical stimulation to trigger motor unit firing and muscular contraction, in alternative embodiments the control data may be generated using muscular contractions generated by voluntary movement by a subject, the volitional movement being controlled in at least one of timing, extent of movement and force of contraction. This is a different type of controlled stimulus than the external electrical stimulus.

In further embodiments the control data may be generated at least in part based on characteristics of MR image data taken from subjects already diagnosed with a muscular abnormality. For example, characteristics of involuntary fasciculations in patients known to have motor neurone disease may be used to filter candidate motor units to confirm that they are detected motor units. Thus the control data to identify the confirmed motor units from the candidate motor units may be generated without using controlled stimulation of muscular contractions in some embodiments.

FIG. 9 is a flow chart schematically illustrating processing performed on MRI images of a time series to identify signal voids potentially associated with motor unit activity. Signal voids are pixels or groups of pixels having much lower MR signal magnitude in a captured MR image than the majority of pixels of an MR image. The signal voids can be seen by visual inspection of the images as shown, for example in FIG. 2a in the region 155. One way of processing MRI images to determine algorithmically which pixels correspond to signal voids caused by motor units firing and triggering muscle contraction is to look at changes over time in the signal value of an image of a muscle region of interest. Since muscle contractions tend to be of short duration changes in a time series of images of the same muscular region are expected to show signal voids appearing and disappearing with a timing that coordinates with motor unit activation, that is, signal voids are transient feature. Since signal voids have characteristically lower signal magnitude than surrounding pixels and lower signal magnitude than the same pixel when the relevant motor unit is not firing, one way of identifying the signal voids is to calculate a mean signal value for a given pixel over time and to look for time instances when the instantaneous signal value is more than a threshold amount or percentage lower than the mean signal value for that pixel or for comparable pixels at different (x,y) positions. Alternatively, a mean signal value of pixels in a given image such as a subset of pixels in a given muscle region may be calculated and signal voids may be identified for individual pixels by comparison with the mean averaged in the (x,y) plane. Other methods of mathematically identifying a low signal value and categorising signal voids may be used.

In the example image processing algorithm represented by the FIG. 9 flowchart, the process begins at element 910 where a time series of MRI images is processed to determine for the plurality of images of the time series a mean signal amplitude for each pixel position (x,y). Thus a mean signal value for a given spatial pixel position is calculated for a time corresponding to at least a part of the time series duration. For example a part of the time series duration where there are expected or known to be no signal voids may be used to calculate a mean pixel value. Next, at process element 920 a variance, $\sigma^2$, and standard deviation, $\sigma$, for each pixel position of interest is calculated. The pixel positions of interest may comprise every pixel in a given MR image or may alternatively comprise a subset of pixels in an image. A larger variance indicates a wider spread in pixel values contributing to the mean and the associated standard deviation can be used to determine which pixels lie furthest from the mean.

At process element 930, the pixels are filtered to identify those pixels having a signal value deviating by more than n times $\sigma$ from the mean, where n is a non-zero integer. In this example n=3, but is not limited to this value. Due to the transient nature of muscle contractions, whilst a given (x,y) position may be categorised as having a low signal value for some images in the time series, it may be categorised as a pixel position having a more average pixel value for other times in the time series. Once the low signal pixels have been identified at process element 930, those low signal pixels are processed at process element 940a to group low signal pixels by spatial connectedness and are processed, in parallel or in series at process element 940b to group low signal pixels by temporal connectedness. Depending on the image capture frequency in a time series relative to an expected muscle fibre response time to motor unit activation, a likely number of temporally contiguous images expected to have low signal value can be predicted. Similarly, a spatial footprint of muscle fibres corresponding to a single motor unit firing may be estimated. In this way pixels having low signal values due to reasons other than motor unit activation can be disregarded. Pixels may have low signal values, for example, due to image aberrations.

At processing element 950 candidate motor units are identified in each MR image of the time series based on the minimum threshold departure from standard deviation (n$\sigma$), the temporal connectedness and the spatial connectedness of the pixel values.

FIG. 9 shows one example flow performed to identify individual motor units in a time series of MRI images. The simplest approach is to take a pixel time series as described with reference to FIG. 9 above and to calculate the variance directly from pixel intensities (signal values) in a time period when there are no motor units firing. This method is most effective when motor unit activity is spare in comparison to a number of time points captured in the image series. This is easier to achieve at earlier stages of a disease such as motor neurone disease but may be more difficult to achieve when processing images form a patient who is at a more advanced stage of the disease when a higher number of motor units per unit area of muscle are likely to be spontaneously firing.

One main source of variance is expected to be due to the inherent noise in the MR image and any one of a number of different approaches may be used to work out what that noise level is. Firing of motor units is expected to cause change in signal level that exceeds any change attributable to inherent noise in the image signal.

According a first approach, a noise level in MR images may be determined by defining a region of a human or animal body that is not muscle and so where there can be no motor unit activity and to use that non-muscle region to calculate the noise variance and then apply that as a uniform value across the MR time series image dataset. This should ideally be an area internal to the object (region of interest), for example an area such as the bone where the scan reconstructs the noise. Within the body there is a signal, outside the body there is no signal but there should be some noise in the background. Areas outside the body may in some image reconstruction methods not contain true noise estimates, being altered by the reconstruction algorithm itself.

According a second approach, a noise level in MR images may be determined by acquiring a DWI scan with the diffusion sensitivity turned off (b value=0 s·mm$^{-2}$). This should ensure that the noise is measured from the time series in the absence of signal voids and may be performed pixelwise.

Figure 10:
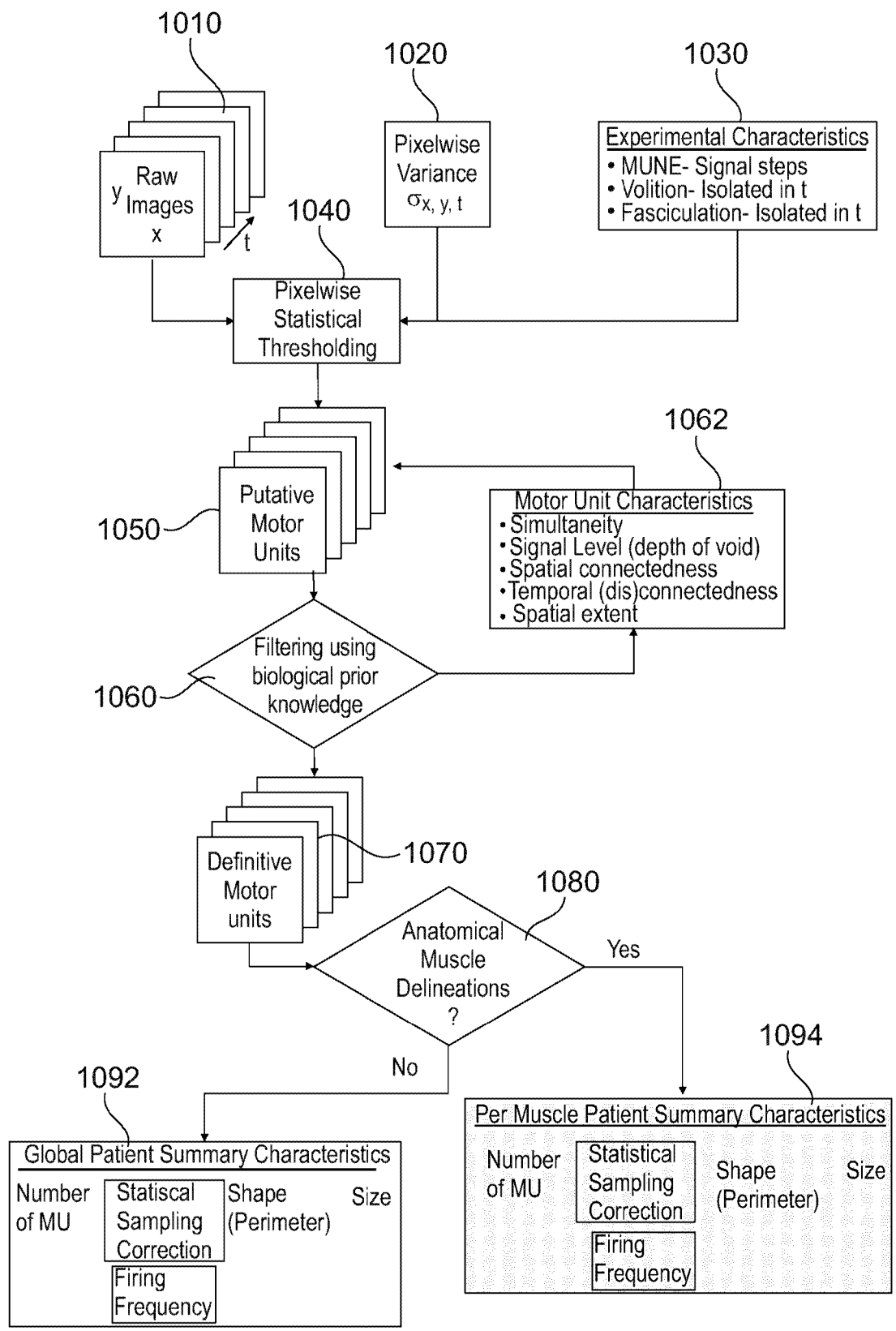
FIG. 10 is a flow chart schematically illustrating an algorithm for processing a time series of MRI images to detect muscular abnormalities.

FIG. 10 is a flow chart schematically illustrating an algorithm for processing a time series of MR images to detect muscular abnormalities. At element 1010 a time series of MR scan images is accessed to process image data. An individual image has pixel values in an x-y plane and corresponds to an instant in time when the image was captured. The duration of the time series and the number of images captured within a given time series are programmable. For example, a time series spanning one or several minutes and comprising, for example, 100 to 200 images. The number of images is selected considering a sample number to give a reliable result statistically. At element 1020 a pixelwise variance may be calculated, for example, as shown in FIG. 9, in which mean pixel values for a given (x,y) position are calculated in a time period assuming that motor unit activation is present in a small number of time samples relative to the total number of samples over which the average is performed. Alternatively the variance may be calculated by determining a mean signal value for a position (x,y) to include time instances when there appear to be no motor units firing. Alternatively, calculating mean signal values for a bone region with diffusion sensitivity turned on or calculating mean signal values in a DWI scan with the diffusion sensitivity set to zero may be used to calculate a pixelwise variance at 1020. At element 1030 experimental characteristics derived from control data may be received or calculated. These experimental characteristics may include at least one of: Motor Unit Number Estimation (MUNE) comprising establishing a relationship between external stimulating current and steps in a number of motor units activated as the current increases; characteristics of signal voids in MR scans where a patient has been asked to voluntarily contract at least one muscle in a region of interest including correlation of timing of the voluntary muscle contractions with a timing of the appearance of any signal voids in the MR scan images; and characteristics of involuntary muscle contractions (fasciculations), which are transient and therefore the effects in the MR scan images may be isolated in time.

The MUNE technique may be based on the identification of successive motor units being activated by an electrical stimulus as the magnitude of the electrical stimulus is increased. As a large number of muscle fibres are known to be controlled by a single motor unit (on the order of hundreds of muscle fibres per motor unit), stimulated activation of successive motor units may control a movement in a large number of muscle fibres resulting in a discrete or discontinuous increase in an MRI image signal intensity. This increase may be identifiable as a step in the MRI signal intensity as a function of the electrical stimulus. The amplitude of the signal step may be used as an indication of a change in signal level expected from a motor unit activity, thus the signal step amplitude may be used to calibrate a threshold level, with respect to the signal noise, in respect to which the depth of a void in the signal can be attributed to the activity of a candidate motor unit.

The experimental characteristics may also comprise a measure of volition. As an alternative to an external electrical stimulus being applied to a nerve of a patient to activate a motor unit, a patient may also trigger an activation of a motor unit by their own volition, that is by voluntarily contracting a muscle. The muscle contraction may be controlled as part of the data collection, for example, by using a strain gauge or a controlled movement of a limb or a controlled timing or a combination of two or more of these factors. By measuring an MR image signal response to a voluntary muscle contraction with respect to time, it may be possible to account for a volition-induced signal void in imaging in order to better isolate spontaneous motor unit activity. Furthermore, during the imaging of the slice of the human body part comprising the muscle region this volition may or may not be required and may occur due to undesirable patient movement, thus the experimental characteristic measured volition signal time response may also be used to isolate volition signals from signal voids attributed to the spontaneous activity of a motor unit, without prior knowledge of the volition's occurrence. This may help to distinguish spontaneous motor unit activity from other activities.

Since all of the muscle fibres controlled by the motor unit may be expected to act similarly with time, i.e. to contract and relax on the same timescale, the depth of a signal void may be expected to scale similarly with time across the entirety of the motor unit area of influence. Thus, the thresholding may be set to consider pixel-to-pixel variation in signal void depth.

At element 1040 pixelwise statistical thresholding is performed using inputs from at least the raw images at element 1010 and possibly using the pixelwise variance calculated at element 1020 and the experimental characteristics of element 1030. According to one example, pixel values differing from the mean value for the given pixel by at least 3 standard deviations are categorised as potentially belonging to a signal void. In this example the threshold value is the mean signal value minus three times the standard deviation, a.

At element 1050 putative motor units identified by the pixelwise statistical thresholding performed at element 1040 are supplied to a filtering algorithm 1060 that filters the putative motor units to disregard any candidate motor units judged as unlikely to be associated with muscle contractions. The filtering of putative motor units may be performed in a cycle comprising elements 1060 and 1062. At element 1062 some example biological filtering criteria are given, which include: looking at simultaneity of pixel positions below the signal level threshold; looking at the depth of the signal void (degree of diminution of the signal value); looking at spatial connectedness of pixels identified as being associated with putative motor units; looking at temporal connectedness of pixels identified as being associated with putative motor units and comparing with an expected variation of signal level with post stimulus response time from the control data (see FIG. 2b); and looking at a spatial extent of groups of pixels identified as putative motor units to compare with an expected spatial extent of a signal void based on control data, noting that the spatial extent may increase as the disease progresses from an early stage to a more advanced stage. The control data set may be obtained from imaging of a patient who has a high probability of having a muscle or nerve disease, or alternatively may be imaged from a patient who has a low probability of having a muscle or nerve disease, e.g. a healthy patient. Thus, the control data set may represent characteristics of healthy motor units or of motor units affected by disease or both.

Therefore, a filtering requirement to validate a candidate motor unit as a confirmed motor unit may consider the simultaneity of the signal change across the pixels classified as one candidate motor unit. For example, a single step down (attenuation) in signal intensity may be expected across all of the pixels associated with a given motor unit, as derived from the control data set. If a gradient or some other difference in signal attenuation across the pixels of the candidate motor unit is detected in the imaging of the candidate motor unit, then the filtering may not validate the candidate motor unit as a confirmed motor unit.

The control data set produced, for example, from the external electrical stimulus of a patient's nerve may also provide calibration data for the filtering at elements 1060 and 1062 to validate candidate motor units by providing information about the expected depths of a signal void associated with a confirmed motor unit. The attenuation of the MRI image signal across all pixels detected as a void in the control data set may demonstrate a characteristic signal void depth, a given decrement in the signal intensity, which may be used to compare at element 1062 the depth of a signal void of a candidate motor unit with the depth of at least one signal void, or a representative signal void, from the control data set. If the depth of the void of a candidate motor unit does not match the signal void depth from the control data set void to within a given level of tolerance, the candidate motor unit may not be validated as a confirmed motor unit and thus be excluded from the definitive motor units selected at element 1070.

Another motor unit characteristic derived from the control data set that may be used for the filter validation at element 1060 is the spatial extent of the motor unit. A range of spatial extent values may be derived from the control data set. This range may be for example an upper and lower extent taken directly from the spatial extents derived from the control data set, or alternatively, the range may be statistically derived from the control data set, where the range may encompass a level of tolerance based on any potential uncertainties or biases in the derived spatial extents of the control data set motor units. A candidate motor unit may not be validated as a confirmed motor unit if its spatial extent does not conform with the range of validation spatial extents set by an analysis of the control data set. Alternatively, it may be that the level of conformity of the candidate motor unit spatial extent with the validation range of spatial extents provides a weighting to be applied to the candidate motor unit during the filtering at element 1060.

A candidate motor unit may be given an overall validation weighting based on a combination of weightings from a comparison between the candidate motor unit characteristics and at least some of the control data set motor unit characteristics. The overall validation weighting may be used to determine if a candidate motor unit is validated as a confirmed motor unit.

Another motor unit characteristic derived from the control data set and used for the filter validation at elements 1060 and 1062 may be the spatial connectedness of the pixels of a candidate motor unit. For example, a candidate motor unit may be detected in a plurality of time-series images. It may be seen from the control data set that the same pixels in an image display signal attenuation when a stimulus is applied to activate a given motor unit over a plurality of separate stimulation events, at different times, i.e. that when a given motor unit is activated the same pixels always display signal attenuation. Alternatively, it may be seen for the control data set that there is a given level of variation in the specific pixels which display attenuation when the same motor unit is repeatedly activated. These pixel spatial characteristics may be used during the filtering of elements 1060 and 1062 to ensure that the spatial connectedness of pixels of a candidate motor unit, if imaged over a plurality of time-series images, are in agreement with the spatial connectedness characteristic derived from the control data set. As described above, the outcome of this spatial connectedness consideration may result in the candidate motor unit not being validated, or alternatively, may contribute to an overall validation weighting for the candidate motor unit.

Another motor unit characteristic derived from the control data set and used for the filter validation at element 1062 may be the temporal disconnectedness of the pixels of a candidate motor unit.

The plurality of motor units controlling a given muscle may overlap in their region of influence over muscle fibres. Thus, if neighbouring motor units spontaneously activate at the same time, then a single candidate motor unit may be classified from the imaging data of that region of muscle, the single candidate motor unit encompassing the area of influence from two or more activated motor units.

It may be evident from the control data set obtained from activating successive motor units by increasing the magnitude of an external electrical stimulus, that a motor unit is represented in MR imaging of the muscle region by a single void. It is also known that the effect of a certain nerve disease, such as motor neuron disease, has an essentially random effect on the spontaneous activation of motor units. Thus, it is unlikely that the neighbouring motor units will spontaneously activate again at the same time. By combining the control data set information with known disease characteristics and analysing the full time-series information for a given signal void, a candidate motor unit may be subdivided into the plurality of underlying voids associated with a plurality of motor units using the temporal disconnectedness. As any given candidate motor unit classified from a signal void detected in one time-series image may be a composite of at least two neighbouring signal voids randomly firing at the same time, if only a part of the void is detected in at least one other time-series of images then the candidate motor unit may be sub-divided into a plurality of candidate motor units based on the area extent of the smallest independently detected part of the candidate motor unit signal void. In this way, individual confirmed motor units may be isolated from groups of spontaneously firing motor units by isolating the individual voids of candidate motor units. Isolating individual confirmed motor units by using the full set of time-series images may provide improved accuracy for motor unit number estimates.

Filtering the candidate motor units using motor unit characteristics derived from the control data set may further increase the accuracy in identifying confirmed motor units as it may prevent false-positive detections or may increase the number of confirmed motor units if the motor unit characteristics empirically derived from the control data set display properties that were not otherwise anticipated. Furthermore, determining an overall validation weighting from a combination of comparisons between the candidate motor unit characteristics and the control data set motor unit characteristics may further improve the accuracy of motor unit detection as by adding more empirically derived constraints to the validation procedure from the control data set, more false-positive motor unit validations can be eliminated.

An outcome of the filtering of the putative motor units identified by signal level thresholding to apply biological prior knowledge and using control data to evaluate characteristics is to narrow down the putative motor units identified from the raw image data at element 1050 to a set of definitive motor units at element 1070. Once the putative motor units have been identified at 1050 there may be a feedback loop which compares what has been identified and could revise the definition of motor units. In a scenario where the raw images capture many motor units firing together, such as potentially in advanced disease states, then it is conceivable that multiple motor units are all detected simultaneously and erroneously become categorised together as a single motor unit. Working on the probability that over time the true motor units are likely to fire asynchronously, the initial motor unit delineation at element 1050 may be revisited by applying the simultaneity and temporal connectedness at element 1062 to identify any appropriate sub-divisions of a given group of low signal value pixels identified as a putative motor unit at 1050 that represent a definitive motor unit at element 1070.

Then at element 1080 it is determined whether or not the muscular abnormality being explored by processing of MR images to determine characteristics of motor units from signal voids may be more effectively explored by performing the analysis on more than one muscle region, that is, by repeating the analysis for two or more different muscle delineations. If only a single muscle delineation is required then analysis data for the definitive set of motor units for the single muscle region is stored in a set of global patient summary characteristics at element 1092. If, on the other hand, two or more muscle delineations are requested to more accurately detect a muscular abnormality then the process proceeds from element 1080 to 1094 where the results of the definitive motor units at element 1070 are stored as a set of per muscle patient summary characteristics. Example summary characteristics for both the global patient summary at 1092 and the per muscle patient summary at 1094 may be a determined number of motor units, a firing frequency of motor units, a shape of motor units, a perimeter of motor units based on the pixels of the associated signal void, and a size of motor units based on the pixels of the associated signal void. A statistical sampling correction may be performed on data corresponding to the definitive motor units to account for the duration of the MRI scan when the sequence is not sensitive to muscle contraction and where motor unit activity may occur but would not be detected.

These properties of the imaged muscle region may be used for the diagnosis of nerve diseases such as motor neuron disease. For example, the effects of a nerve disease, such as motor neuron disease, may increase the occurrence of random fasciculations in the muscle. The analysis of the confirmed motor unit firing frequency may help to identify the presence of this disease characteristic in a patient. Motor neuron disease may also negatively impact the health of a motor unit such that as a motor unit becomes diseased its connection with its associated muscle fibres degrades and a neighbouring motor unit may establish new connections with the muscle fibres. Thus, a nerve disease such as motor neuron disease reduces the number of motor units and increases the size of the remaining motor units. An analysis of the number and size of motor units may provide an indication of disease which may be used for diagnosis. In comparison with existing diagnosis techniques such as electromyography (EMG), the accuracy of the motor unit analysis can be increased using the technique described by FIG. 10 by the execution of the machine-readable instructions as a much larger area of the patient can be sampled, for example entire limbs, with higher levels of sampling completeness and more precise identification of individual motor units. This is also more time efficient than traditional EMG techniques. This technique also eliminates the need for invasive procedures to be performed on the patient in order to determine motor unit properties, such as the insertion of probes required by EMG.

The increased area of sampling provided by the technique described by FIG. 10 by the execution of the machine-readable instructions may provide a significant increase in the time efficiency of a subsequent diagnosis as the technique allows a plurality of muscle types to be analysed from a single time-series of images. The processing of images to identify confirmed motor units and to determine properties of those motor units could subsequently contribute to a diagnosis of a muscular abnormality such as motor neurone disease.

Figure 11:
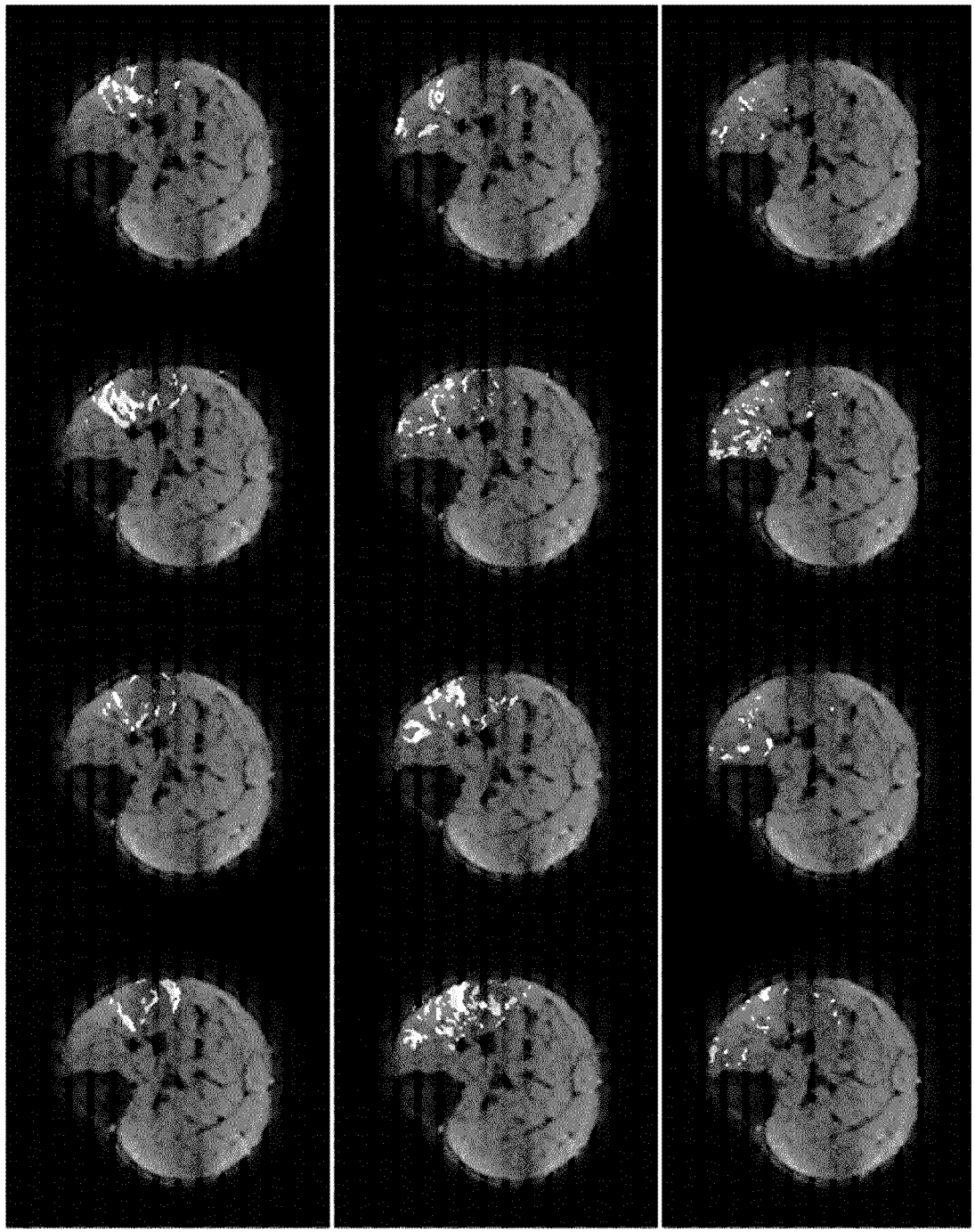
FIG. 11 is a series of MRI scan images showing motor unit activity throughout a tibialis anterior muscle upon peroneal nerve stimulation by an external electrical stimulus.

FIG. 11 is a series of MRI scan images showing motor unit activity throughout a tibialis anterior muscle upon peroneal nerve stimulation by an external electrical stimulus. In this series of images signal voids are represented by the white pixels. In this series of images the muscle pixels activate as the stimulus current is increased and as successive new motor units reach their respective activation thresholds. Individual motor neurons interface (synapse) to many muscle fibres distributed over a relatively wide area in order to generate an evenly spread contraction throughout the muscle. FIG. 11 shows a distributed pattern of signal voids throughput the tibialis anterior muscle region upon peroneal nerve stimulation. As the stimulation current increases, the signal voids are seen to expand to encompass new areas of inter-digitated muscle reflecting successive new motor units reaching their respective activation thresholds.

Figure 12:
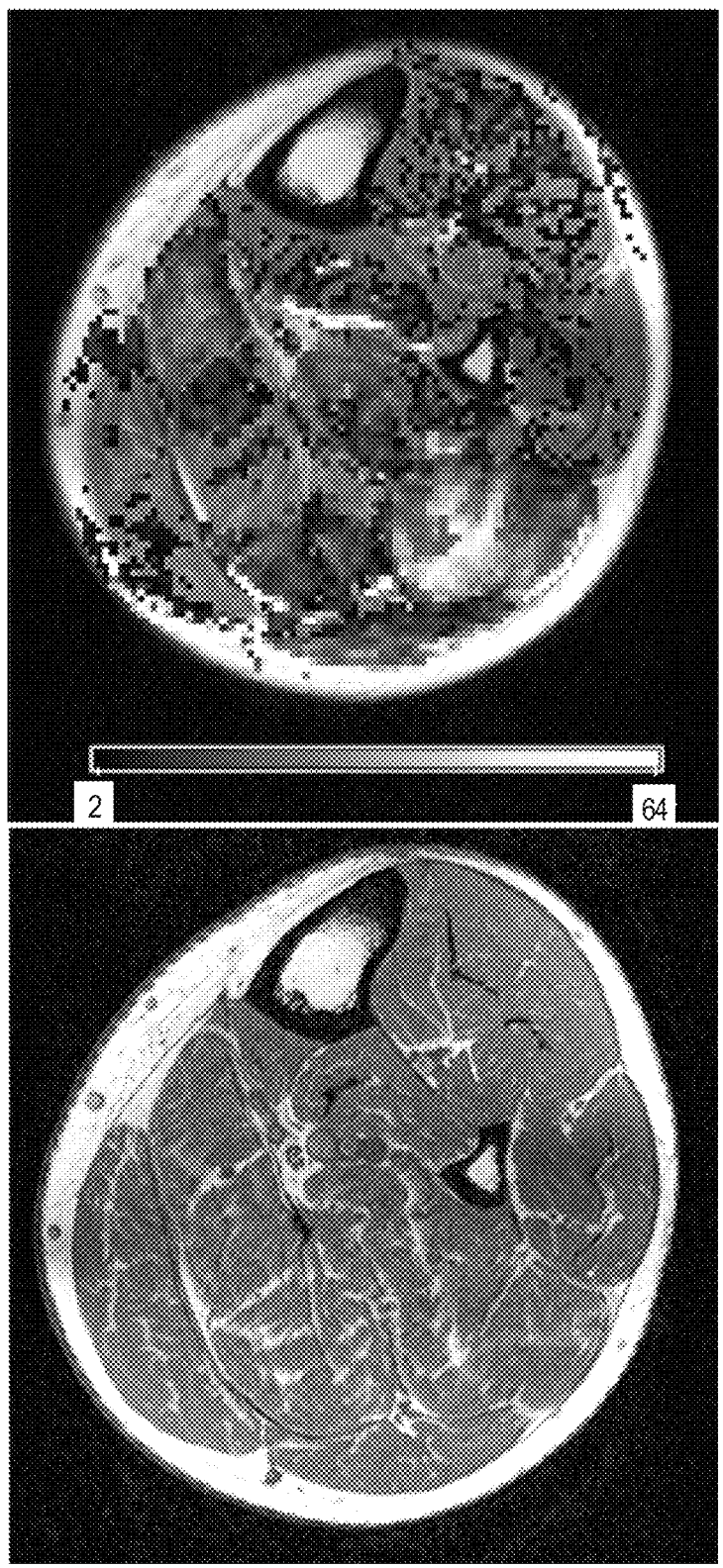
FIG. 12 schematically illustrates a spatial pattern of motor unit activity in a patient whose muscles have not been externally stimulated or voluntarily contracted, the activity being revealed via a pattern of signal voids detected by processing a time series of MRI images, the motor unit activity being indicative of muscle abnormalities.

FIG. 12 schematically illustrates a spatial pattern of motor unit activity in a patient whose muscles have not been externally stimulated or voluntarily contracted, the activity being revealed via a pattern of signal voids detected by processing a time series of MRI images, the motor unit activity being indicative of muscle abnormalities. The right-hand image of FIG. 12 shows a total number of fasciculations detected over a three minute time series of motor unit MRI images. The signal voids in the image represent a widespread patent of motor unit activity within a soleus muscle of the lower leg. The widespread motor unit activity was found despite the patient having no clinical signs of fasciculation. This indicates that analysis of signal voids in MRI images could lead to earlier detection of muscle abnormalities caused by diseases such as motor neurone disease (or equivalently ALS).

Figure 13:
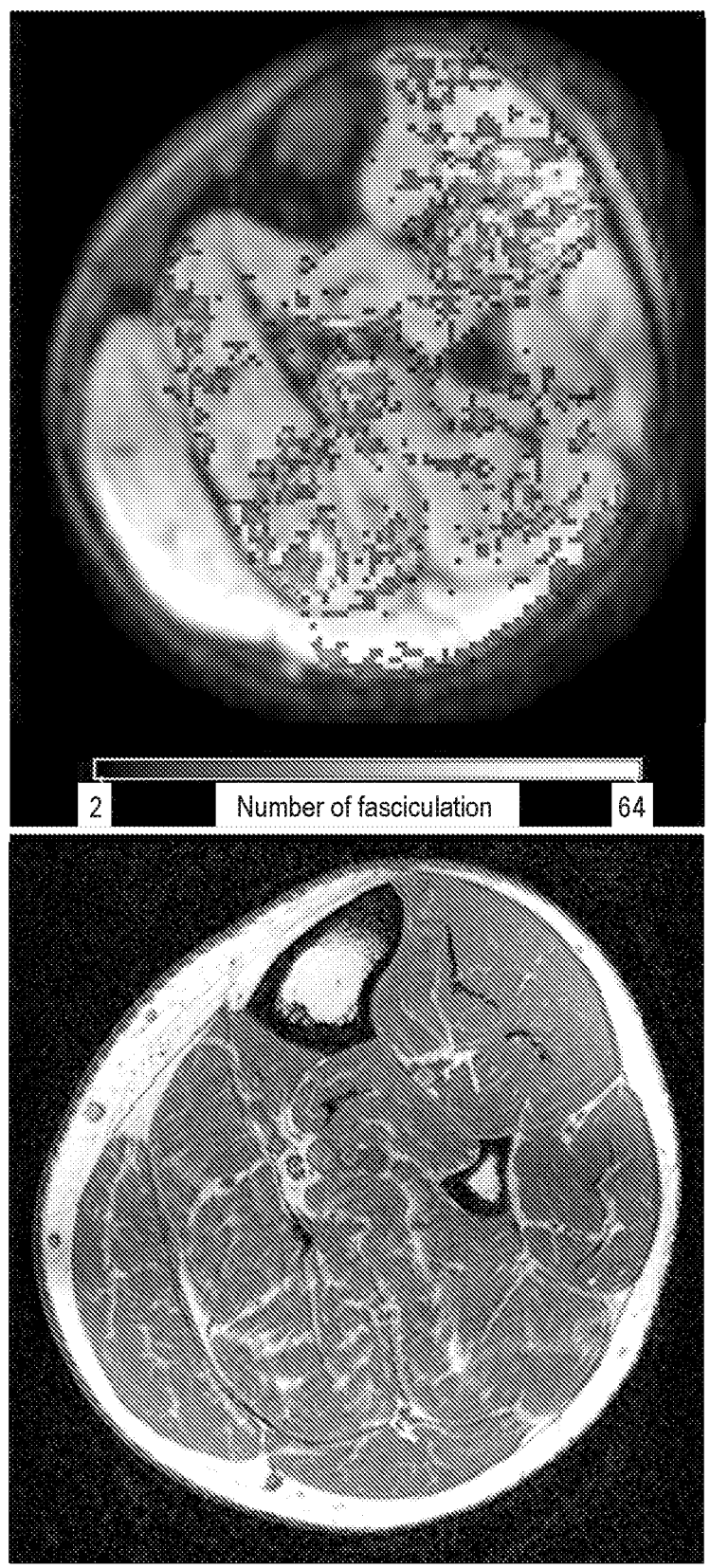
FIG. 13 schematically illustrates motor unit activity during volitional muscle contraction in the same patient who was the subject of the FIG. 13 scan.

FIG. 13 schematically illustrates motor unit activity during volitional muscle contraction (dorsiflexion) in the same patient who was the subject of the FIG. 12 scan revealed via a pattern of signal voids detected by processing a time series of MRI images. In this example, the motor unit activity was captured from a one minute time series of MR images collected while the subject was raising their toes. Increased motor unit activity can be seen in the tibealis anterior although there is decreased spontaneous activity in the soleus relative to FIG. 13.

As described above, neuromuscular diseases can lead to characteristic changes in the anatomy of motor units (MU). According to the present technique an Magnetic Resonance approach to image motor unit activity has been developed. In-scanner electrical stimulation of MU was synchronized to a pulsed-gradient spin-echo imaging sequence sensitive to microscopic contraction of muscle fibre. Experimental data was compared to a simple theoretical model and scan parameters were evaluated. The spatial pattern of muscle fibres innervated by different MU was imaged for the first time in healthy controls. The results described herein have demonstrated that diffusion imaging can be used to measure motor unit activity. Data is consistent with the signal mechanism being a simple contraction of the muscle during the diffusion sensitive period of the scan and shows that b-values above 50 s·mm−2 do not provide additional contrast. This method potentially allows the distribution of motor units to be visualized in a way which is currently not possible by any other means.

Using in-bore electrical stimulation, the empirical results described herein demonstrate all the characteristics expected of motor unit activity being found in the signal voids of MR scan images and thus help to validate diffusion MRI as a method to non-invasively assess motor unit activity.

In this description where functional units have been described as circuitry, the circuitry may be general purpose processor circuitry configured by program code to perform specified processing functions. The circuitry may also be configured by modification to the processing hardware. Configuration of the circuitry to perform a specified function may be entirely in hardware, entirely in software or using a combination of hardware modification and software execution. Program instructions may be used to configure logic gates of general purpose or special-purpose processor circuitry to perform a processing function.

Circuitry may be implemented, for example, as a hardware circuit comprising custom Very Large Scale Integrated, VLSI, circuits or gate arrays, off-the-shelf semiconductors such as logic chips, transistors, or other discrete components. Circuitry may also be implemented in programmable hardware devices such as field programmable gate arrays, FPGA, programmable array logic, programmable logic devices, A System on Chip, SoC, or the like.

Machine readable program instructions may be provided on a transitory medium such as a transmission medium or on a non-transitory medium such as a storage medium. Such machine readable instructions (computer program code) may be implemented in a high level procedural or object oriented programming language. However, the program(s) may be implemented in assembly or machine language, if desired. In any case, the language may be a compiled or interpreted language, and combined with hardware implementations. Program instructions may be executed on a single processor or on two or more processors in a distributed manner.

For the purposes of the description, a phrase in the form "A/B" or in the form "A and/or B" means (A), (B), or (A and B). For the purposes of the description, a phrase in the form "at least one of A, B, and C" means (A), (B), (C), (A and B), (A and C), (B and C), or (A, B and C).

The invention claimed is:

1. Machine readable instructions stored on a non-transitory machine readable medium, the machine readable instructions upon execution to cause processing circuitry to:
receive a time series of Magnetic Resonance, MR, images representing a slice of a body part;
analyze the time series of images to identify one or more signal voids in one or more images of the series, a signal void being a localized region of signal attenuation;
correlate the identified signal voids with candidate motor units of skeletal muscle, wherein the correlation comprises performing a comparison of at least one characteristic of the identified signal voids in the images with a control data set of MR images produced by applying a controlled stimulus to a motor nerve in control subjects to establish inherent characteristics of signal voids corresponding to motor units of skeletal muscle, the comparison to generate confirmed motor units; and
analyze properties of candidate motor units validated via the comparison as confirmed motor units and determine at least one of: a firing frequency of at least one of the confirmed motor units, a size of at least one of the confirmed motor units, a number of confirmed motor units in a given image area or a shape of at least one of the confirmed motor units.

2. The machine readable instructions as claimed in claim 1, wherein the control data set of MR images is generated by progressively increasing a magnitude of an external electrical stimulus applied to a predetermined motor nerve of a human or animal body.

3. The machine readable instructions as claimed in claim 2, comprising discriminating between different motor units of skeletal muscle based on discontinuities in pixel intensity as the external electrical stimulus is increased.

4. The machine readable instructions as claimed in claim 1, wherein identifying signal voids in one or more images of the series of MR images comprises determining a threshold signal level for distinguishing a signal void from signal noise.

5. The machine readable instructions as claimed in claim 4, wherein the threshold signal level determination for a healthy motor unit of skeletal muscle is based on a signal variance of pixel values of at least a subset of images of the time series.

6. The machine readable instructions as claimed in claim 5, wherein the threshold signal level determination is determined depending on variance of pixel values of MR images of a non-muscle region of a subject.

7. The machine readable instructions as claimed in claim 5, wherein the threshold signal level determination is determined depending on variance of pixel values of diffusion weighted MR images of a region of interest with the diffusion sensitivity turned off.

8. The machine readable instructions as claimed in claim 1, wherein the MR images are generated using either a phase contrast imaging technique or using a diffusion weighted imaging technique.

9. The machine readable instructions as claimed in claim 1, wherein the control data set is generated using a diffusion weighted imaging technique having b value in a range of between 10 and 50 seconds per $mm^2$ or having a b value in a range between 100 and 200 seconds per $mm^2$.

10. The machine readable instructions as claimed in claim 1, wherein the control data set is generated by initiating image capture of the slice of the human body part at a predetermined time delay with respect to an application of a controlled electrical stimulus to a motor nerve.

11. The machine readable instructions as claimed in claim 10, wherein the predetermined time delay is set based on a known muscle response characteristic of a healthy skeletal muscle or a diseased skeletal muscle.

12. The machine readable instructions as claimed in claim 1, comprising using at least one of the determined properties of the confirmed motor units to make a diagnosis of a muscular abnormality.

13. The machine readable instructions as claimed in claim 1, wherein the validation of confirmed motor units from candidate motor units comprises filtering of the candidate motor units based on at least one of: simultaneity of the detected signal voids, a depth of the detected signal voids relative to other pixel values, spatial connectedness of the detected signal voids, temporal connectedness of the detected signal voids and a spatial extent of the detected signal voids.

14. A data processing apparatus having one or more processors comprising:
circuitry to receive a time series of Magnetic Resonance, MR, images representing a slice of a body part;

circuitry to analyze the time series of images to identify one or more signal voids in one or more images of the series, a signal void being a localized region of signal attenuation;

circuitry to correlate the identified signal voids with candidate motor units of skeletal muscle, wherein the correlation comprises performing a comparison of at least one characteristic of the identified signal voids in the images with a control data set of MR images characterizing inherent properties of signal voids corresponding to motor units of skeletal muscle; and circuitry to analyze properties of candidate motor units validated via the comparison as confirmed motor units and determine at least one of: a firing frequency of at least one of the confirmed motor units, a size of at least one of the confirmed motor units, a number of confirmed motor units in a given image area or a shape of at least one of the confirmed motor units.

15. The data processing apparatus as claimed in claim 14, wherein identifying signal voids in one or more images of the series of MR images comprises determining a threshold signal level for distinguishing a signal void from signal noise.

16. The data processing apparatus as claimed in claim 14, wherein the threshold signal level determination is based on a signal variance of pixel values of at least a subset of images of the time series.

17. The data processing apparatus as claimed in claim 14, wherein the threshold signal level is determined depending on a variance of pixel values of MR images of a non-muscle region of a subject.

18. The data processing apparatus as claimed in claim 14, wherein the threshold signal level determination is determined depending on variance of pixel values of diffusion weighted MR images of a region of interest with the diffusion sensitivity turned off.

19. The data processing apparatus as claimed in claim 14, wherein identifying signal voids in one or more images of the series of MR images comprises determining a threshold signal level for distinguishing a signal void from signal noise.

20. A method of processing images to determine one or more properties of skeletal muscle, the method comprising:

receiving a time series of Magnetic Resonance, MR, images representing a slice of a body part;

analyzing the time series of images to identify one or more signal voids in one or more images of the series, a signal void being a localized region of signal attenuation;

correlating the identified signal voids with candidate motor units of skeletal muscle, wherein the correlation comprises performing a comparison of at least one characteristic of the identified signal voids in the images with a control data set of MR images to validate at least a subset of the candidate motor units as confirmed motor units; and analyzing properties of the confirmed motor units to determine at least one of: a firing frequency of at least one of the confirmed motor units, a size of at least one of the confirmed motor units, a number of confirmed motor units in a given image area or a shape of at least one of the confirmed motor units.

\* \* \* \* \*